United States Patent
Shibazaki et al.

(10) Patent No.: US 7,224,826 B2
(45) Date of Patent: May 29, 2007

(54) FLUORESCENT INTENSITY MEASURING METHOD AND APPARATUS

(75) Inventors: Takami Shibazaki, Hachioji (JP); Kaneyasu Okawa, Tsukui-gun (JP)

(73) Assignee: Olympus Corporation, Tokyo (JP)

( * ) Notice: Subject to any disclaimer, the term of this patent is extended or adjusted under 35 U.S.C. 154(b) by 584 days.

(21) Appl. No.: 10/606,518

(22) Filed: Jun. 26, 2003

(65) Prior Publication Data

US 2004/0001196 A1   Jan. 1, 2004

Related U.S. Application Data

(63) Continuation of application No. PCT/JP01/10029, filed on Nov. 16, 2001.

(30) Foreign Application Priority Data

Dec. 26, 2000 (JP) ............................. 2000-395882
Nov. 7, 2001 (JP) ............................. 2001-342190

(51) Int. Cl.
    *G06K 9/00* (2006.01)
(52) U.S. Cl. ...................... 382/128; 382/274; 382/275; 422/82.07; 422/82.08; 436/172
(58) Field of Classification Search ................ 382/128, 382/141–152, 254, 274, 275; 356/317, 318, 356/417, 517; 250/458.1, 459.1, 461.1, 461.2; 422/82.07, 82.08; 436/172
See application file for complete search history.

(56) References Cited

U.S. PATENT DOCUMENTS 5,880,473 A   3/1999   Ginestet 6,262,837 B1 *   7/2001   Nagano et al. ............. 359/368

FOREIGN PATENT DOCUMENTS

| JP | 61-159936 | 7/1986 |
|---|---|---|
| JP | 01-292238 | 11/1989 |
| JP | 7-31160 | 11/1995 |
| JP | 2000-121559 | 4/2000 |
| JP | 2000-292353 | 10/2000 |
| WO | WO 98/07022 | 2/1998 |
| WO | WO 00/05571 | 2/2000 |

OTHER PUBLICATIONS

International Preliminary Examination Report with Translation of International Application No. PCT/JP01/10029.

* cited by examiner

*Primary Examiner*—Matthew C. Bella
*Assistant Examiner*—Shefali Patel
(74) *Attorney, Agent, or Firm*—Scully, Scott, Murphy & Presser, P.C.

(57) ABSTRACT

A fluorescent image is obtained by emitting the light with a wavelength which excites a labelling fluorescent substance, a mask is created by a foreign matter area image extracted from an image of foreign matter adhering to the measurement object obtained by emitting light with a wavelength which does not excite the fluorescent substance, and logical multiplication of the mask and the fluorescent image is executed, thereby obtaining a fluorescent image that a foreign matter area is eliminated from the fluorescent image.

42 Claims, 12 Drawing Sheets

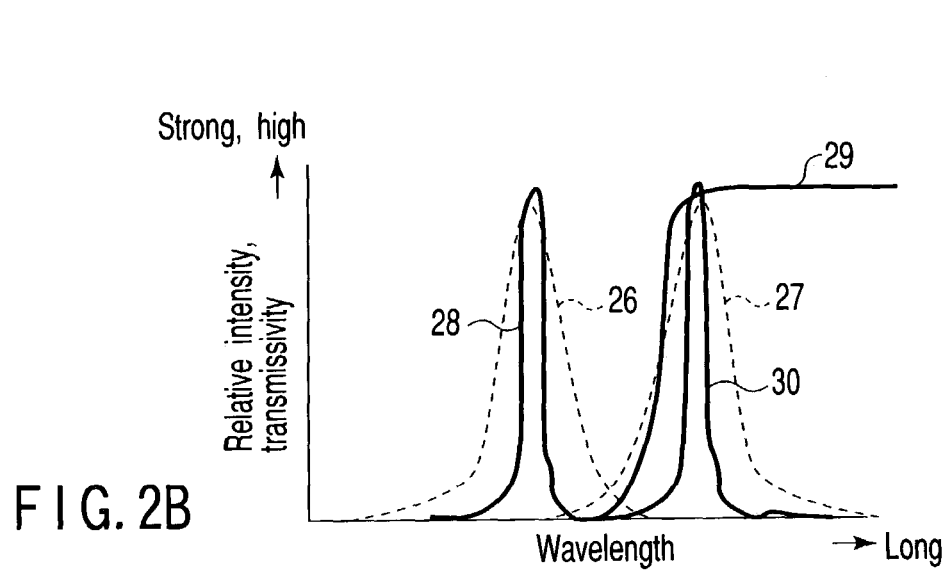
FIG. 2A
FIG. 2B
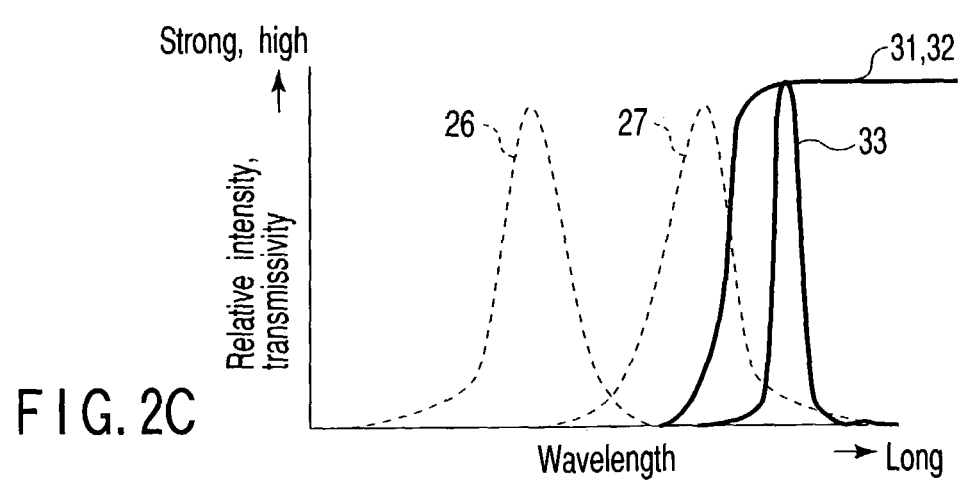
FIG. 2C

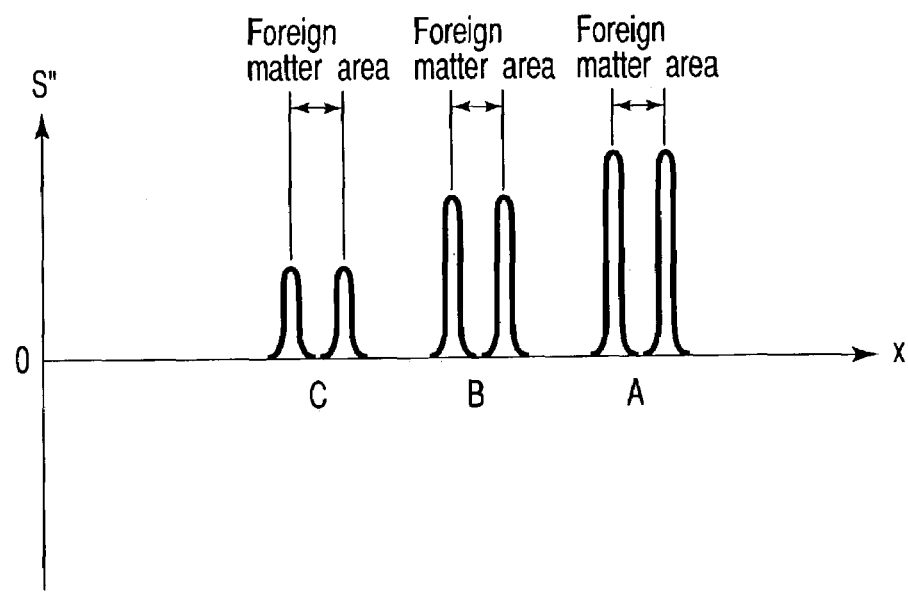
F I G. 10
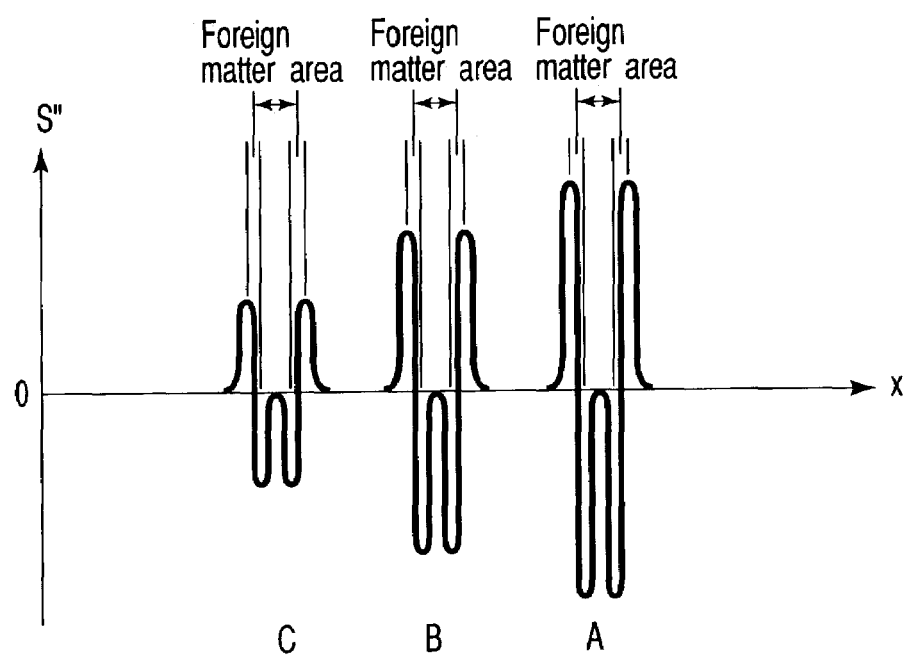
F I G. 11

FLUORESCENT INTENSITY MEASURING METHOD AND APPARATUS

CROSS-REFERENCE TO RELATED APPLICATIONS

This is a Continuation Application of PCT Application No. PCT/JP01/10029, filed Nov. 16, 2001, which was not published under PCT Article 21(2) in English.

This application is based upon and claims the benefit of priority from the prior Japanese Patent Applications No. 2000-395882, filed Dec. 26, 2000; and No. 2001-342190, filed Nov. 7, 2001, the entire contents of both of which are incorporated herein by reference.

BACKGROUND OF THE INVENTION

1. Field of the Invention

The present invention relates to an apparatus which aims at a plurality of minute points arranged on a plane and measures the intensity of each minute point, and more particularly to a fluorescent intensity measuring method and apparatus suitable for a system which aims at a bio chip in which substances such as DNAs or proteins labelled by a fluorescent substance are arranged on a plane as minute points with a high density and performs fluorescence analysis.

2. Description of the Related Art

For example, Jpn. Pat. Appln. KOKAI Publication No. 2000-121559 discloses an apparatus which measures a fluorescent intensity of each minute point.

FIG. 17 is a schematic block diagram showing a fluorescent intensity measuring apparatus disclosed in Jpn. Pat. Appln. KOKAI Publication No. 2000-121559. The fluorescent intensity measuring apparatus disclosed in this publication is constituted by a chip drive portion 503 which scans in a direction Y in the drawing, a bio chip 520 in which samples subjected to fluorescence labelling are formed on a substrate surface as minute points, a laser 506 as an excitation light source, the laser beam is reflected by the mirror 580 toward a dichroic mirror 508 which reflects a laser beam from the laser 506 and transmits therethrough the fluorescence from the measurement object, a condenser lens 509, a head drive portion 502 which scans in a direction X in the drawing, a read head 507 including the condenser lens 509 and the dichroic mirror 508, a dichroic mirror 511 which separates the fluorescence from the minute points in accordance with each wavelength, filters 515 and 519 which separate the laser beam and the fluorescence, aperture lenses 514 and 518, pin-hole plates 513 and 517, and photomultipliers 512 and 516.

The effects of the fluorescent intensity measuring apparatus having such a structure are as follows. That is, the laser beam generated by the laser 506 is reflected by the mirror 580 toward the dichroic mirror 508 and is reflected by the dichroic mirror 508 and directed to the condenser lens 509. Then, it is condensed on the bio chip 520, thereby forming a laser beam spot. At this moment, when a fluorescent substance exists in a part irradiated with the laser beam spot, the fluorescent substance is excited by the laser beam, and the fluorescence is generated. The generated fluorescence is condensed by the condenser lens 509, then transmitted through the dichroic mirror 508, separated by the color separation dichroic mirror 511 in accordance with each wavelength, condensed by the aperture lenses 514 and 518 in accordance with each wavelength, transmitted through the pin-hole plates 513 and 517, and enters the photomultipliers 512 and 516. The photomultipliers 512 and 516 are sensors which detect photons and convert them into pulses on a TTL level, and hence the light which has entered the photomultipliers 512 and 516 becomes a pulse signal, and the fluorescent intensity of the minute point can be measured by measuring the pulse number. Further, if the above-described operation is carried out while mechanically scanning the laser beam spot by a chip drive portion 503 and a head drive portion 502, the fluorescent intensity of the minute points on the entire bio chip 520 is measured.

However, if foreign matter which reflects the excitation light or generates the fluorescence exists on the surface of the bio chip 520, the light which becomes the noise from the foreign matter is detected as well as the fluorescence from the spot 521 on the bio chip 520, and hence it is impossible to cope with occurrence of an error in the measured intensity.

Furthermore, since the prior art fluorescent intensity measuring apparatus cannot judge presence/absence of foreign matter, a quantitative judgment cannot be made with respect to the reliability of an intensity value of the minute points.

In view of the above-described problems, it is an object of the present invention to provide a fluorescent intensity measuring method and apparatus which can reduce measurement errors even if foreign matter exists in the vicinity of the surface of a bio chip, and can recognize the existence of foreign matter and make a quantitative judgment of the reliability of an intensity measurement value.

BRIEF SUMMARY OF THE INVENTION

To achieve this aim, according to the present invention, there is provided a fluorescent intensity measuring method which measures the intensity of minute points including a fluorescent substance which are arranged on a substrate having a substantially flat surface, comprising:

a first imaging step of emitting light with a wavelength with which the fluorescent substance can be excited and obtaining an image of the minute point including the fluorescent substance as a first image;

a second imaging step of obtaining as a second image an image of foreign matter which has adhered on the substrate by light having a wavelength which does not excite the fluorescent substance;

an extraction step of obtaining a binarized image by extracting a foreign matter area from the second image; and a foreign matter elimination step of disabling an image at a part overlapping the foreign matter area in the first image by using the binarized image as a mask.

Moreover, according to the present invention, there is provided a fluorescent intensity measuring apparatus which measures the intensity of a fluorescent image obtained by irradiating minute points which are arranged on a substrate having a substantially flat surface and include a fluorescent substance with an excitation light, comprising:

a light source;

first wavelength selecting means for selecting a wavelength of the excitation light;

image forming means for forming an image of the fluorescent substance;

second wavelength selecting means for selecting only a wavelength of a generated fluorescence;

photoelectric converting means for obtaining an image by scanning a fluorescent image;

storing means for storing the image; and image processing means for performing:

processing to emit light having a wavelength which can excite the fluorescent substance in the light from the light source by controlling the first wavelength selecting means, to obtain an image of the minute point including the fluorescent substance as a first image by the photoelectric converting means by controlling the second wavelength selecting means, and to store the first image in the storing means;

processing to emit light with a wavelength which does not excite the fluorescent substance in the light from the light source by controlling the first wavelength selecting means, to obtain an image of foreign matter which has adhered to the substrate by the photoelectric converting means by controlling the second wavelength selecting means, and to store the second image in the storing means;

processing to obtain a binarized image by extracting a foreign matter area from the second image stored in the storing means; and processing to disable an image at a part overlapping the foreign matter area in the first image stored in the storing means with the binarized image being used as a mask.

That is, according to the fluorescent intensity measuring method and apparatus of the present invention, light with a wavelength with which the fluorescent substance can be excited is emitted and an image of the minute point including the fluorescent substance is obtained as a first image, a mask is created based on the foreign matter area image extracted from an image of the foreign matter which has adhered to the measurement object obtained by light having a wavelength which does not excite the fluorescent substances, and a logical product of the mask and the first image is obtained, thereby eliminating the foreign matter area from the first image. Therefore, the noise light from the foreign matter which has adhered to the bio chip can be removed.

BRIEF DESCRIPTION OF THE SEVERAL VIEWS OF THE DRAWING

FIG. 2A is a view showing an example of a spectral characteristic of a relative intensity of an absorption wavelength and a fluorescent wavelength of a fluorescent substance for use in a bio chip;

FIG. 2B is a view showing a spectral transmissivity characteristic of a fluorescent measurement filter unit;

FIG. 2C is a view showing a spectral transmissivity characteristic of a foreign matter image shooting filter unit;

FIG. 10 is a view showing a differential signal S" relative to a pixel position in the direction x at a position where the foreign matter exists in the direction y in cases where the first order differential operator is used when obtaining the differentiation signal by another technique;

FIG. 11 is a view showing a differential signal S" relative to a pixel position in the direction x at a position where the foreign matter exists in the direction y in cases where the second order differential operator is used when likewise obtaining the differential signal by another technique;

DETAILED DESCRIPTION OF THE INVENTION

Preferred embodiments according to the present invention will now be described hereinafter with reference to the accompanying drawings.

FIRST EMBODIMENT

A fluorescent intensity measuring method and apparatus according to a first embodiment of the present invention will be first described with reference to FIGS. 1 to 13B.

Figure 1:
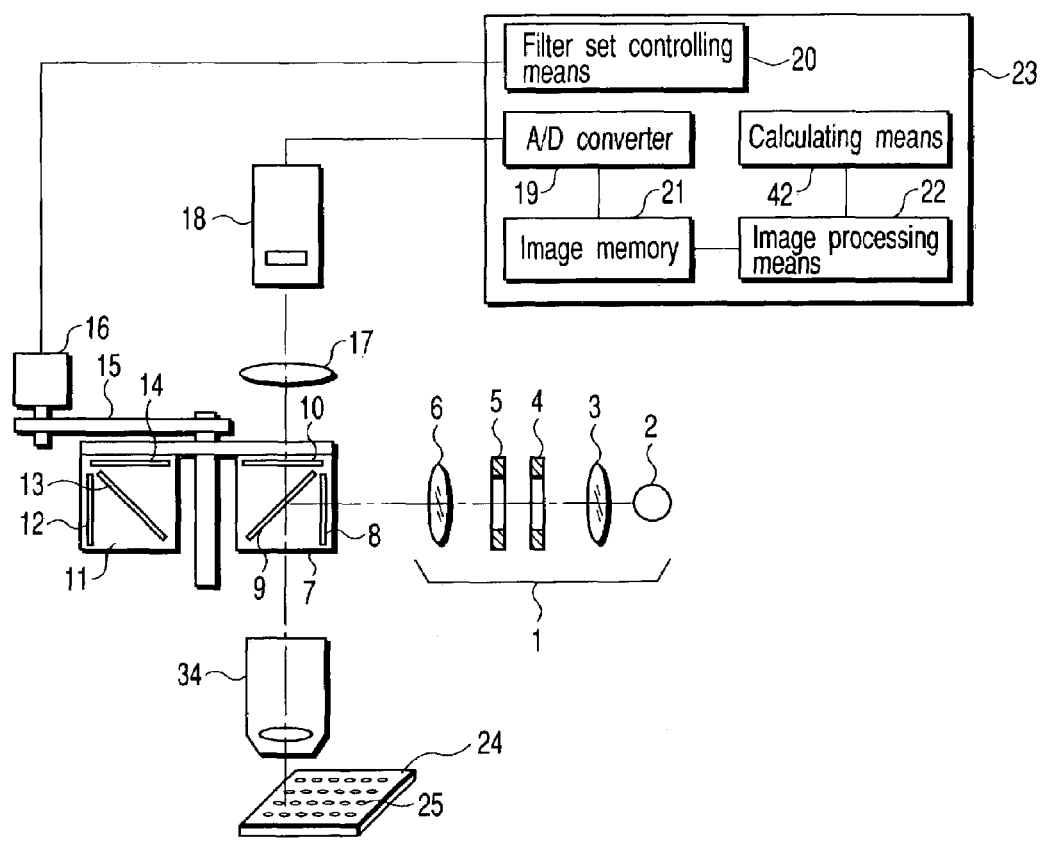
FIG. 1 is a block diagram showing an outline of a fluorescent intensity measuring apparatus according to a first embodiment of the present invention.

As shown in FIG. 1, in a fluorescent intensity measuring apparatus according to this embodiment, an illumination unit 1 has a light source 2 such as a mercury lamp, and a light flux projected from this light source 2 is condensed by a collector lens 3, stopped down by an aperture diaphragm 4 and a field diaphragm 5, and then enters a filter set 7 through a lens 6.

Further, in this embodiment, a fluorescent substance having such a characteristic as shown in FIG. 2A is used as a labelling material. That is, in this drawing, it has such an absorption spectrum as indicated by reference numeral 26 and a light emission spectrum 27 having a longer wavelength than that of the absorption spectrum.

The fluorescent measurement filter set 7 is, as shown in FIG. 2B, constituted by a wavelength selection filter 8 (which will be referred to as an excitation filter hereinafter) having a spectral transmittance characteristic which selectively transmits therethrough a wavelength of the light with which the fluorescent substance used as the labelling substance and having the characteristic shown in FIG. 2A is excited, a dichroic mirror 9 having a spectral characteristic 29 which reflects the light having the wavelength transmitted by the excitation filter 8 and transmits therethrough only a wavelength of the fluorescence generated from the labelling fluorescent substance of minute points on the bio chip with a fixed wavelength band, and a wavelength selection filter 10 (which will be referred to as an absorption filter hereinafter) having a spectral transmittance characteristic 30 which selectively transmits therethrough only the wavelength of the fluorescence generated from the labelling fluorescent substance of the minute points on the bio chip and absorbs unnecessary wavelength components.

Furthermore, a foreign matter image shooting filter set 11 is, as shown in FIG. 2C, constituted by a wavelength selection filter 12 having a spectral transmittance characteristic 31 which does not excite the fluorescent substance used as the labelling substance and selectively transmits therethrough the light having the wavelength which is reflected by a foreign matter on the bio chip or by which the foreign matter generates the fluorescence, a dichroic mirror 13 having a spectral characteristic 32 which reflects the light transmitted by the wavelength selection filter 12 and transmits therethrough the fluorescence generated by the foreign matter on the bio chip or the light reflected by the foreign matter, and a filter 14 having a spectral characteristic 33 which selectively transmits therethrough only the fluorescence generated from the foreign matter or the wavelength of the light reflected by the foreign matter.

The filter sets 7 and 11 are attached to a filter set attachment member 15. One of the filter sets is arranged in such a manner that an intersection of an illumination optical axis and an observation optical axis matches with the dichroic mirrors 9 and 13, and these filter sets are configured so as to be switched by a filter set switching mechanism 16 based on a switching signal from later-described filter set controlling means 20.

Figure 3:
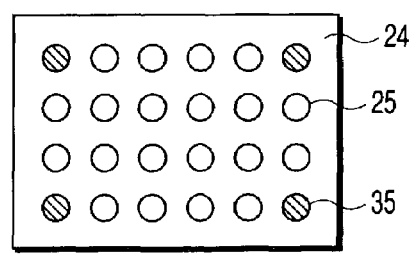
FIG. 3 is a schematic view showing a format of the bio chip.

As shown in FIG. 3, the bio chip 24 is formed of, e.g., a glass plate having a square shape of 10 mm×20 mm, and objects such as a DNA or a protein labelled by a fluorescent substance, e.g., FITC (fluorescein isothiocyanate) or rhodamine are arranged in the grid form at intervals of, e.g., 100 μm as minute points 25 each having a diameter of, e.g., 50 μm and a small substantial circular shape. Moreover, for the purpose of recognizing an area in which the minute points are formed, four sets of the fluorescent substance used for labelling are formed at corner portions as position detection minute points 35. In addition, this bio chip 24 is provided on a non-illustrated two-axial (XY) stage, can move in a horizontal plane and can be positioned within a view field of an object lens 34.

The object lens 34 is arranged above the bio chip 24 at an operation distance, and an observation light path is formed in such a manner that the fluorescence generated by causing excitation and illumination of the bio chip 24 is condensed through the object lens 34 and an image of the bio chip 24 is formed on a CCD element 18 as a photoelectric conversion element through an image formation lens 17. As an example of such an apparatus, a general incident-light fluorescence microscope can be used. It is to be noted that a coaxial incident-light illumination is adopted as an illumination method in this embodiment, but an oblique incident-light illumination can be used away from the observation light path an a dark field incident-light illumination can be also used by utilizing the illumination light as an orbicular zone.

The CCD element 18 electrically scans a fluorescent image of the bio chip 24 and outputs an analog image signal. Controlling means 23 has an A/D converter 19 which converts this analog signal into digital data and an image memory 21, and is constituted by image processing means 22 having a binarization function for images, a function to perform logical multiplication between a plurality images, a function to measure an area of an arbitrary area and a function to integrate an intensity value in an arbitrary area, calculating means 42 for performing four arithmetic operations, and filter set controlling means 20.

Effects of this embodiment will now be described with reference to FIGS. 1 to 13B.

First, the bio chip 24 is positioned by a non-illustrated two-axial stage in such a manner that a measurement range specified by four positioning minute points 35 on the bio chip 24 matches with a view field range determined by an image magnification of an observation optical system and a light receiving surface size of the CCD element 18. Then, the fluorescent measurement filter set 7 is positioned at a shooting position by the filter set switching mechanism 16 so as to shoot a fluorescent image of the minute points 25 on the bio chip 24.

On the other hand, the light flux emitted from the light source 2 is condensed by the collector lens 3, stopped down by the aperture diaphragm 4 and the field diaphragm 5, and then led to the fluorescent measurement filter set 7 through the lens 6. The light led to the fluorescent measurement filter set 7 becomes the light flux with a wavelength having a specific half band width by the excitation filter 8 having the spectral transmittance characteristic 28 matching with the absorption wavelength band 26 of the labelling fluorescent substance (which will be referred to as the excitation light hereinafter). Since the dichroic mirror 9 has the spectral characteristic 29, this light flux is reflected by the dichroic mirror 9 and emitted onto the bio chip 24 through the object lens 34. At this moment, the fluorescent substance arranged as the minute points 25 on the bio chip 24 generates fluorescence with a longer wavelength than that of the excitation light which is determined by its physical properties and environment. Since the fluorescence generated from each minute point 25 is condensed by the object lens 34 and the fluorescent generated here has a transmission wavelength band of the dichroic mirror 9, it is transmitted through the dichroic mirror 9 of the fluorescent measurement filter set 7, and further transmitted through the absorption filter 10, thereby forming an image of the minute points 25 on the CCD element 18.

Thereafter, the image of the minute points 25 on the CCD element 18 is electrically scanned by the CCD element 18 and converted into an analog electrical signal. This analog signal is converted into a digital signal by the A/D converter 19, and stored in an image memory 21 as a fluorescent image 101 of the minute point shown in FIG. 4.

Figure 4:
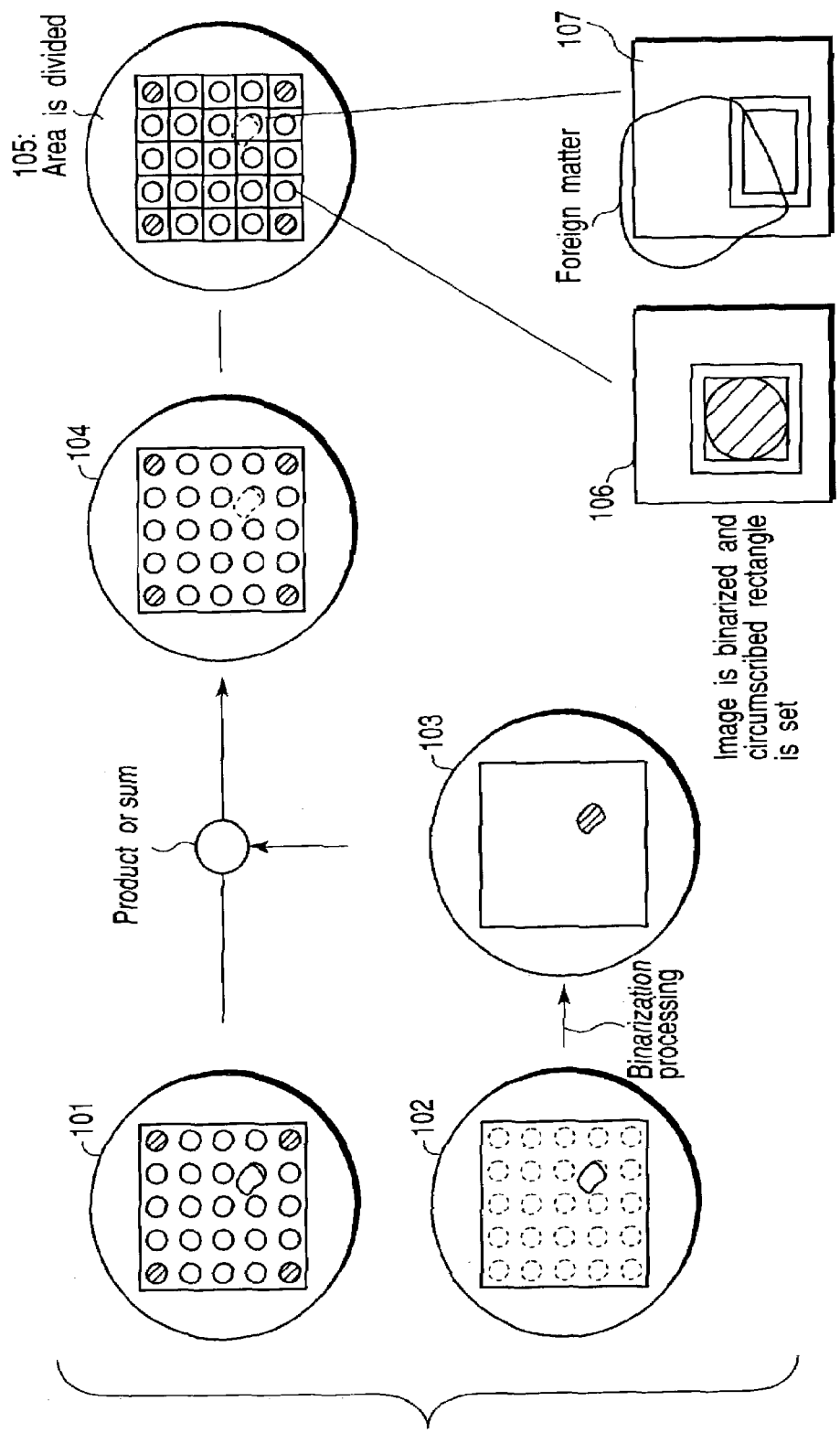
FIG. 4 is a schematic view showing a data processing method when measuring the intensity of minute points in the first embodiment.

Then, the fluorescent measurement filter set 7 is switched to the foreign matter image shooting filter set 11 by the filter set switching mechanism 16, the illumination light having a light wavelength by which the fluorescent substance is not excited is supplied to the bio chip 24, and a foreign matter image 102 shown in FIG. 4 is stored in the image memory 21 by the operation equal to the above-described step. At this moment, since the labelling fluorescent substance of the minute point 25 is not excited, the image of the minute point 25 is not included in the foreign matter image 102.

Subsequently, in order to extract the foreign matter area from the foreign matter image 102, the binarization processing is performed with respect to the foreign matter image 102 by image processing means 22. At this moment, generally, when an image of an object having the uniform intensity is formed on the light receiving element having a γ value "1" by an aplanatic lens, a boundary of the image obtained by binarization with ½ of the maximum intensity of the image determined as a threshold value can be considered as an intersection of a main light beam and an optimum image surface, and the obtained binarized area can be adopted as an outer shape of the foreign matter.

However, if there are spatial irregularities in the excitation light with which the bio chip 24 is irradiated, spatial irregularities also exist in the intensity of the fluorescence generated by the foreign matter. Further, provided that ½ of the maximum intensity is a threshold value without variation, even if a plurality of the same foreign matters exist, some of the foreign matters cannot be recognized as the foreign matters due to spatial irregularities in the excitation light.

Figure 5B:
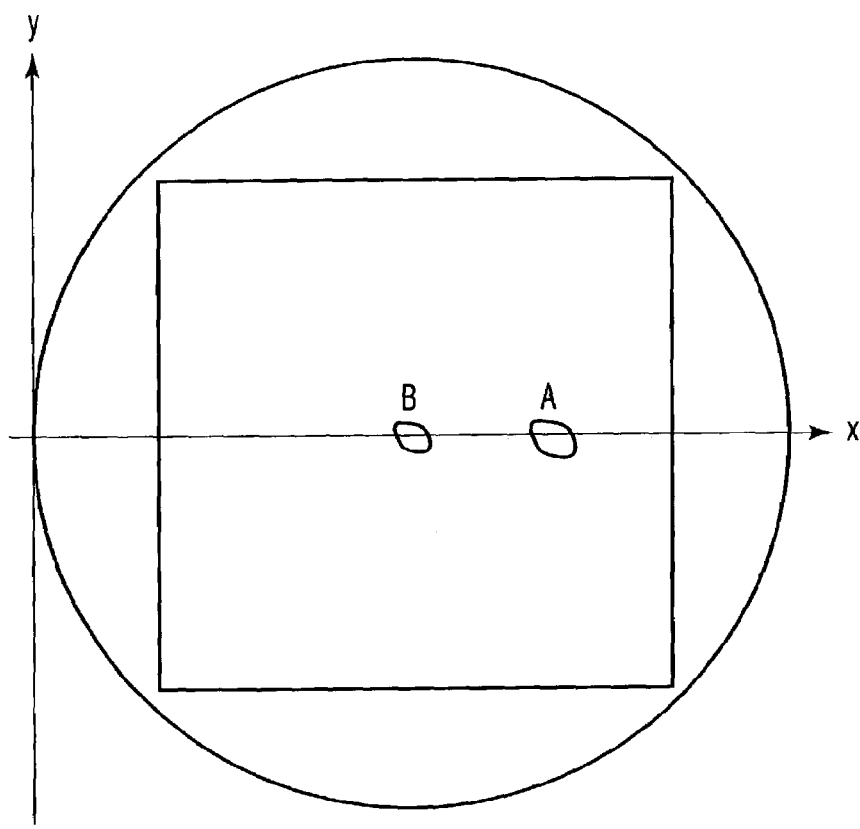
FIG. 5B is a view showing a binarization result provided that ½ of the maximum intensity $S_{max}$ is a threshold value.
Figure 5A:
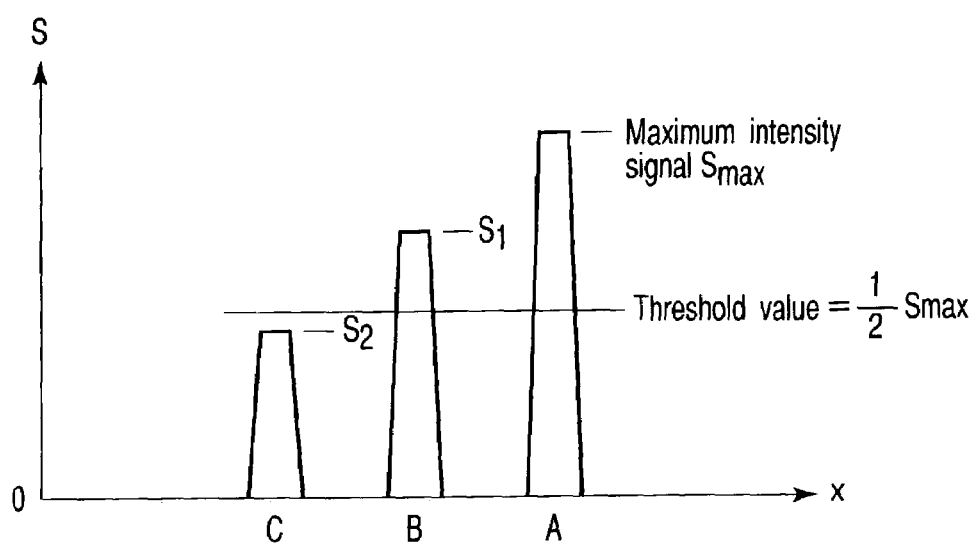
FIG. 5A is a view showing an intensity signal S relative to a pixel position in a direction x at a position where a foreign matter exists in a direction y.
Figure 6:
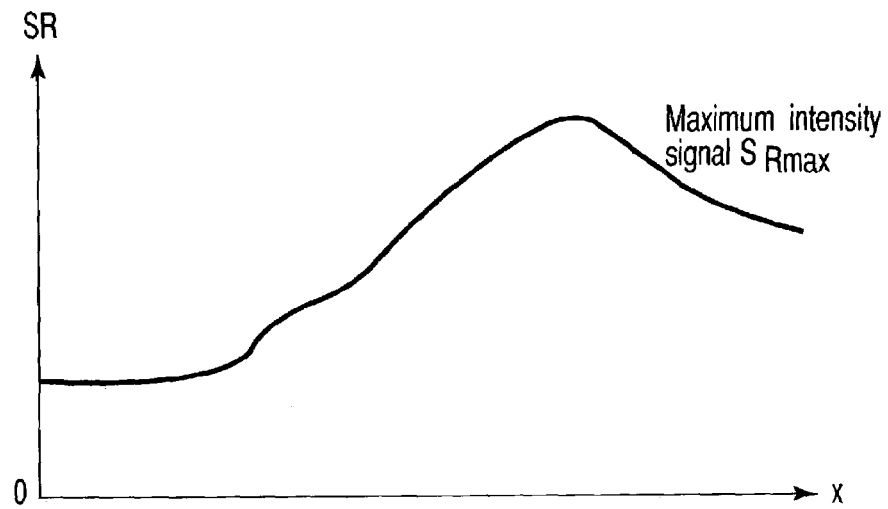
FIG. 6 is a view showing an intensity distribution characteristic of a reference image.

This phenomenon will now be described in detail with reference to FIGS. 5A and 5B. FIG. 5A is a view showing an intensity signal S relative to a pixel position in a direction x at a position where the foreign matters exist in a direction y. As shown in the drawing, in cases where spatial irregularities exist in the excitation light, when a plurality of foreign matters (in the drawing, three foreign matters A, B and C exist) having the same characteristic exist, the same intensity signal cannot be obtained. Assuming that $S_{max}$ is an intensity signal of the foreign matter A which is largest, $S_1$ and $S_2$ are respectively intensity signals of the foreign matter B and the foreign matter C and $S_{max}/2 < S_1 < S_{max}$ and $S_2 < S_{max}/2$ are achieved, when it is determined that ½ of the maximum intensity is a threshold value without variation, only the boundary of the foreign matter A obtained by binarization matches with an intersection of the main light beam and the optimum image surface as shown in FIG. 5B, and an accurate area is shown. However, in case of the foreign matter B, the shown area is smaller than the accurate area. Furthermore, in case of the foreign matter C, the area is not recognized at all.

A method of eliminating this drawback will now be described.

Figure 7B:
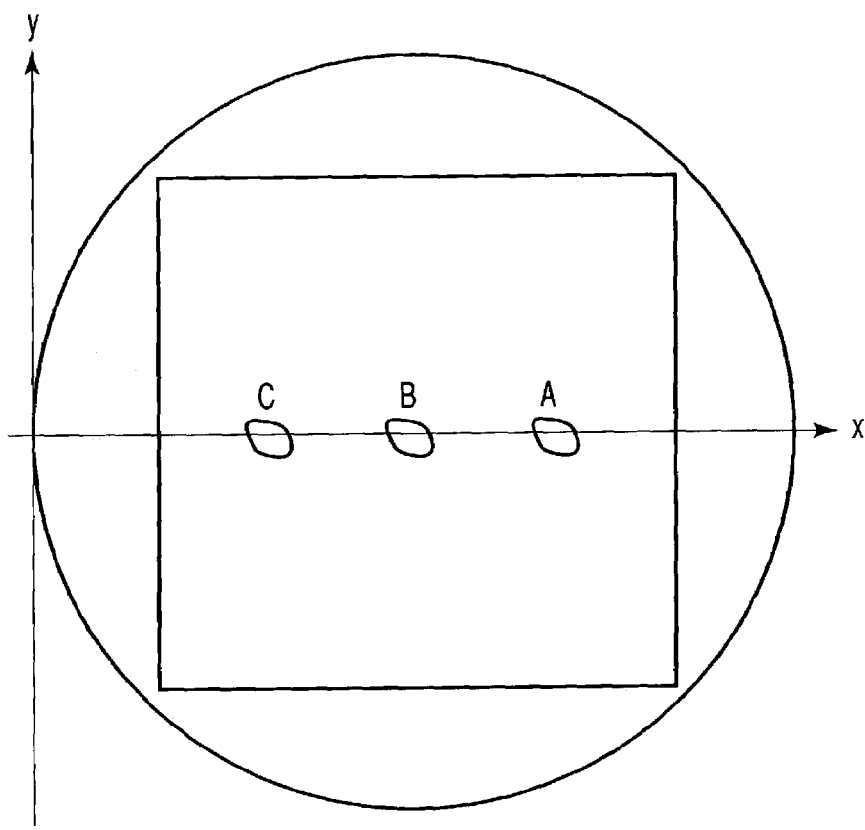
FIG. 7B is a view showing a binarization result provided that ½ of a maximum value $S'_{max}$ is a threshold value.
Figure 7A:
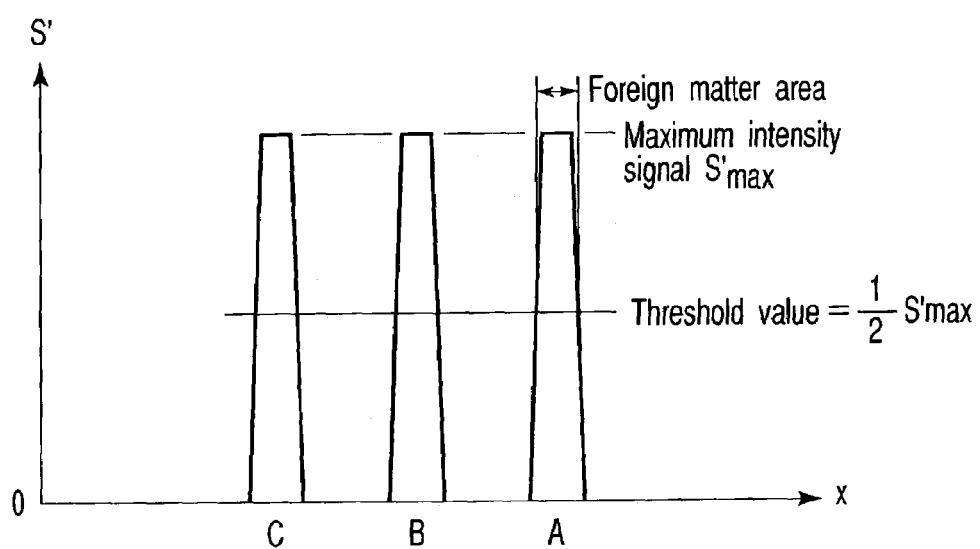
FIG. 7A is a view showing an intensity signal S' relative to a pixel position in the direction x at a position where the foreign matter exists in the direction y provided that a value obtained by multiplying the intensity signal in FIG. 5A by a ratio $S_{Rmax}/S_R$ of the maximum intensity signal $S_{Rmax}$ relative to the reference intensity signal SR is an intensity signal S'.

A first method is measuring irregularities in the excitation light and performing correction based on this measurement. In order to carry out this method, an image (reference image) of a flat surface plate having a uniform reflectivity or light emission ratio is imaged as an intensity distribution characteristic such as shown in, e.g., FIG. 6 (it is actually a two-dimensional intensity distribution but it is shown as a one-dimensional distribution for the convenience's sake in this example). It is to be noted that the vertical axis represents a reference intensity signal $S_R$ and its maximum value is a maximum intensity signal $S_{Rmax}$ in FIG. 6. Then, when a value obtained by multiplying the intensity signal S obtained as shown in FIG. 5A by $S_{Rmax}/S_R$ is determined as an intensity signal S', the intensity signals S' of the three foreign matters become equal to each other as shown in FIG. 7A. Therefore, provided that ½ of the maximum value $S'_{max}$ of the intensity signal S' is a threshold value in place of using the intensity signal S, the boundary of each of the three foreign matters obtained by binarization matches with the intersection of the main light beam and the optimum image surface as shown in FIG. 7B, and the correction area is shown. Although description has been given with the intensity of parts other than the foreign matters being determined as 0, noises may be mixed due to the stray light or the dark current of the light receiving element in some cases, and hence it is more desirable to determine the threshold value as $(S'_{min}+S'_{max})/2$. Here, $S'_{min}$ is a minimum value of the intensity signal S'.

Description will now be given as to a second method of eliminating this drawback. This method is different from the above-described first method and requires no reference image.

That is, it is assumed that the intensity signal S is expressed as f(i, j), and a differentiation signal S" is calculated by using the following expression.

$$S'' = \frac{g(i, j)}{\sum_{m=-m_1}^{m_2} \sum_{n=-n_1}^{n_2} C_{0,m,n} f(i+m, j+n)}$$

Here, the vicinities of (i, j) in a direction i and a direction j (which is not restricted to adjacent pixels) can be represented by $[-m_1, m_2]$ and $[-n_1, n_2]$, respectively. Moreover, $C_{0, m, n}$ is an average operator. Usually, the following expression can be given.

$$C_{0,m,n} = \frac{\begin{bmatrix} 1 & 1 & 1 \\ 1 & 1 & 1 \\ 1 & 1 & 1 \end{bmatrix}}{9} \text{ or } \frac{\begin{bmatrix} 1 & 2 & 1 \\ 2 & 4 & 2 \\ 1 & 2 & 1 \end{bmatrix}}{16}$$

In addition, g(i, j) represents a differentiation image, and it can be represented by the following expression.

$$g(i, j) = \sum_{m=-m_1}^{m_2} \sum_{n=-n_1}^{n_2} C_{m,n} f(i+m, j+n)$$

or $$g(i, j) = \left| \sum_{m=-m_1}^{m_2} \sum_{n=-n_1}^{n_2} C_{1,m,n} f(i+m, j+n) \right| + \left| \sum_{m=-m_1}^{m_2} \sum_{n=-n_1}^{n_2} C_{2,m,n} f(i+m, j+n) \right|$$

Here, $C_{m, n}$, $C_{1, m, n}$ and $C_{2, m, n}$ are differential operators. For example, as a first order differential operator, the following expression can be often used.

$$C_{1,m,n} = \begin{bmatrix} -1 & 0 & 1 \\ -1 & 0 & 1 \\ -1 & 0 & 1 \end{bmatrix}, C_{2,m,n} = \begin{bmatrix} -1 & -1 & -1 \\ 0 & 0 & 0 \\ 1 & 1 & 1 \end{bmatrix}$$

or $$C_{1,m,n} = \begin{bmatrix} -1 & 0 & 1 \\ -2 & 0 & 2 \\ -1 & 0 & 1 \end{bmatrix}, C_{2,m,n} = \begin{bmatrix} -1 & -2 & -1 \\ 0 & 0 & 0 \\ 1 & 2 & 1 \end{bmatrix}$$

As a second order differential operator, the following expression which is also known as a Laplacian filter is often used.

$$C_{m,n} = \begin{bmatrix} 0 & 1 & 0 \\ 1 & -4 & 1 \\ 0 & 1 & 0 \end{bmatrix} \text{ or } C_{m,n} = \begin{bmatrix} 1 & 1 & 1 \\ 1 & -8 & 1 \\ 1 & 1 & 1 \end{bmatrix}$$

Figure 8:
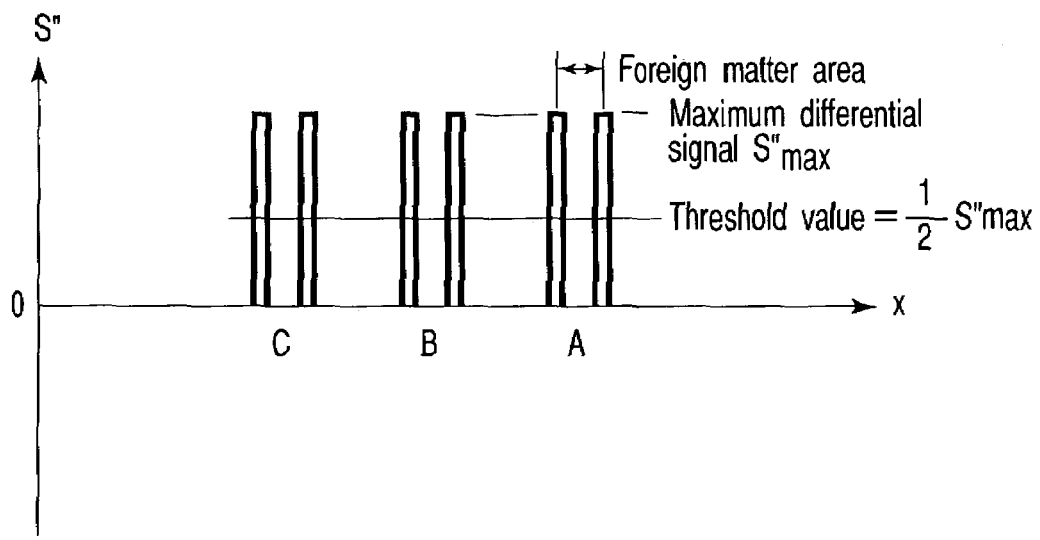
FIG. 8 is a view showing a differential signal S" relative to a pixel position in the direction x at a position where the foreign matter exists in the direction y when a first order differential operator is used.
Figure 9:
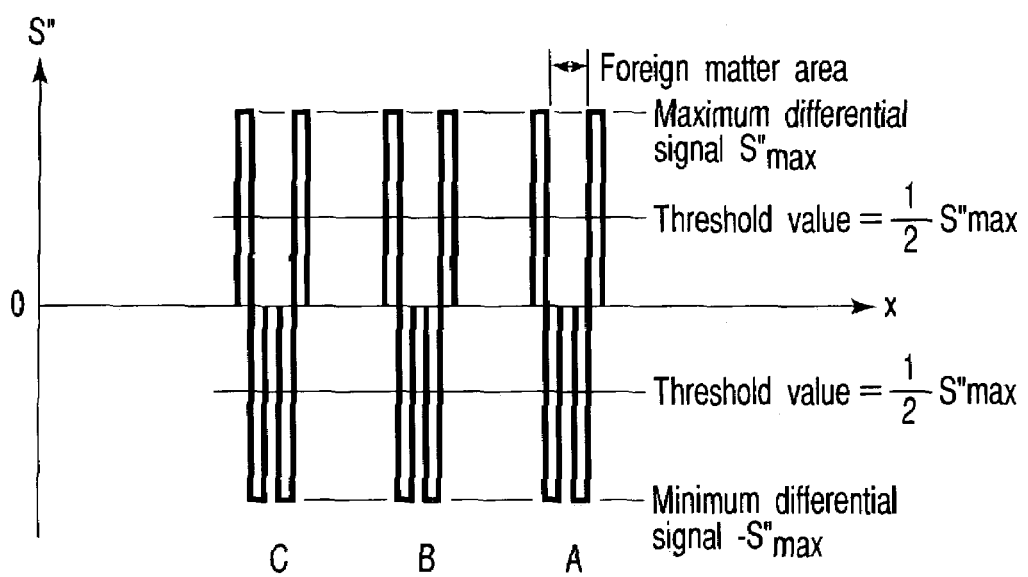
FIG. 9 is a view showing a differential signal S" relative to a pixel position in the direction x at a position where the foreign matter exists in the direction y when a second order differential operator is used.

The differentiation signal S" obtained in this manner is a differentiation signal which is the same with respect to the three foreign matters as shown in FIG. 8 when the first order differential operator is used, and a contour line of each foreign matter is a line having a fixed width with the maximum differentiation signal $S''_{max}$. The line connecting the center of this width becomes an actual foreign matter contour line. Additionally, in case of using the second order differential operator, as shown in FIG. 9, the three foreign matters have the same differential signal, and the line connecting points at which the positive and negative of the differential signal S" are inverted becomes the foreign matter contour line.

It is to be noted that description has been given as to each case that the inclination of the vicinity of the boundary of the intensity signal S is constant for the convenience's sake, but actually this inclination is not constant. Therefore, the pattern of the differential signal S" in FIGS. 8 and 9 is not a rectangular distribution but it is close to a normal distribution, and hence it is desirable to determine the foreign matter area by using a signal processed with the threshold value or determine the foreign matter area by using a peak point of the differential signal S". In the former case, however, the threshold value does not have to be ½ of the maximum differential signal $S''_{max}$ in principle. Further, in the latter case, the following expression can suffice instead of using the above-described expression which obtains the differential signal S".

$$S'' = g(i,j)$$

That is, it is as shown in FIGS. 10 and 11. In FIG. 10, an area formed by points corresponding to the maximal value of S" is determined as the foreign matter area. In FIG. 11, an area formed by each central point between a point corresponding to the maximal value of S" and a point corresponding to the minimal value of the same is determined as the foreign matter area.

A method of setting a further appropriate threshold value in the former case will now be described.

Figure 12:
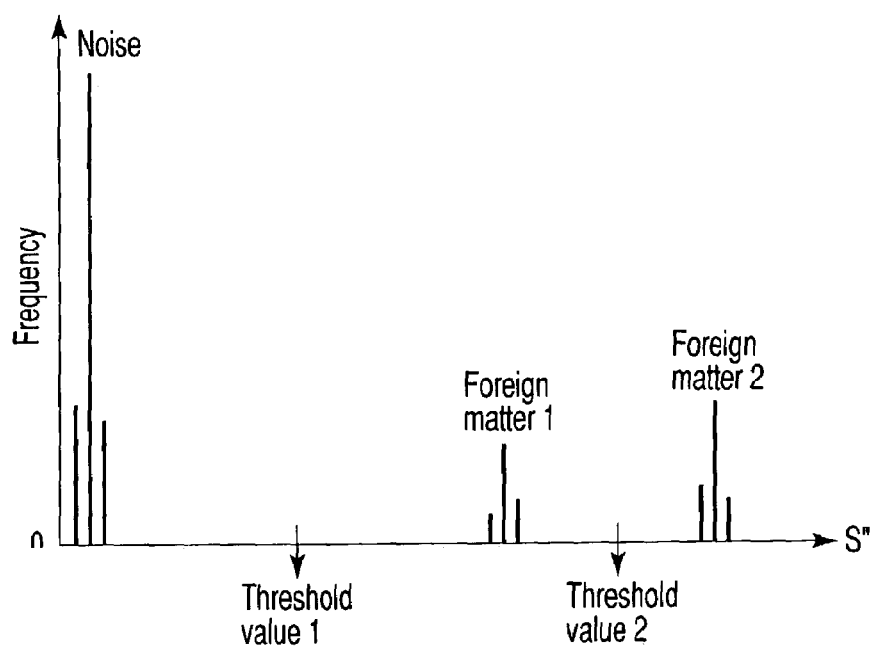
FIG. 12 is a frequency distribution view for explaining a method of setting an appropriate threshold value when two kinds of foreign matters exist, in which a horizontal axis represents a representative value of the evenly divided differentiation signal S" and a vertical axis represents a sum total of pixels corresponding to this differential signal S"

That is, the above has described the same one type of the foreign matter, but actually a plurality of kinds of foreign matters exist. Description will now be given as to a method of setting an appropriate threshold vale when a foreign matter 1 and a foreign matter 2 exist. FIG. 12 is a frequency table in which a horizontal axis represents a representative value of the evenly divided differential signal S" and a vertical axis represents a sum total of pixels corresponding to the differentiation signal S" (which will be referred to as a frequency hereinafter). As shown in the drawing, noise intensively appears in a zone where the differential signal S" is small, and the foreign matter 1 and the foreign matter 2 sporadically appear in an inherent zone in accordance with their characteristics. Therefore, the threshold value can be set by using this frequency table. That is, when the threshold value 1 shown in the drawing is adopted, the contour lines of the foreign matter 1 and the foreign matter 2 can be obtained. When the threshold value 2 is adopted, the contour line of the foreign matter 2 can be obtained. Furthermore, when the threshold value 1 and the threshold value 2 are adopted, the contour line of only the foreign matter 1 can be obtained.

At last, the contour line of the foreign matter and its inside being determined as, e.g., 0 or −1 and any other part being determined as 1 are stored in the image memory as a foreign matter area image 103 by the image processing means 22.

Moreover, as to the fluorescent image 101 of the minute point 25, the foreign matter area image 103 is used as a mask, a product of two images is taken by the image processing means 22, and a fluorescent image 104 of the minute point 25 from which the foreign matter area is removed is obtained. That is, it is possible to obtain the fluorescent image 104 that the area having the value of 0 or −1 can be recognized as the foreign matter area.

In addition, in this example, the area obtained by the binarization processing is directly adopted as the foreign matter area, and it is removed from the fluorescent image 101 of the minute point 25. However, with respect to the foreign matter area obtained by binarization, as a sum of a distance from the center of a diffraction image and a valley of the second order diffraction peak and the third order diffraction peak (a blur quantity generated due to diffraction, the first term on the right side of the following expression (1)) and a maximum blur quantity obtained when taking a focusing error into consideration (the second term on the right side of the expression (1)), an optical blur quantity is given by the following expression (1), and the foreign matter area may be expanded by this quantity and removed from the fluorescent image of the minute point. However, β is an image magnification of the optical system, λ is a wavelength of the light forming an image of the foreign matter, α is the numerical aperture of the object lens 34 on the bio chip side, and Δ is a defocusing amount.

$$\delta = \beta \cdot \left(1.619 \frac{\lambda}{\alpha} + \alpha |\Delta|\right) \quad (1)$$

Then, the position detection minute points 35 formed on the bio chip 24 are detected, positions of the gravitational center of four position detection minute points 35 or centroids of the binarized images of the position detection minute points 35 are obtained, and the fluorescent image 104 of the minute points is divided into each minute point unit as indicated by reference numeral 105 based on this coordinate and arrangement information of the bio chip 24.

Then, a measurement area relative to each minute point 25 is set by the following procedure.

Figure 13A:
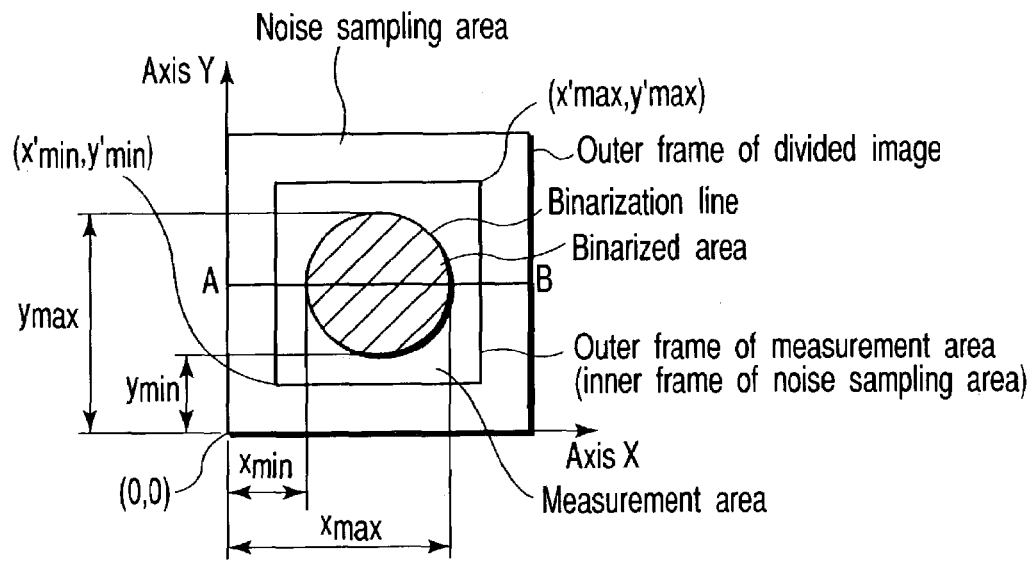
FIG. 13A is a view showing a divided image relative to one minute point.

That is, with respect to the divided images 106 and 107 for each minute point from which the foreign matter area is removed, ½ of the maximum intensity in the divided image or an average value of the maximum intensity and the minimum intensity is determined as a threshold value, and binarization processing is carried out. Then, a maximum X coordinate, a minimum X coordinate, a maximum Y coordinate and a minimum Y coordinate of the binarized area are obtained, and they are determined as $x_{max}$, $x_{min}$, $y_{max}$ and $y_{min}$. Based on these coordinates, two coordinates which give rectangular areas used to determine a measurement area and a noise sampling area are given as $(x'_{min}, y'_{min})$ and $(x'_{max}, y'_{max})$ as shown in FIG. 13A by the following expressions.

$$x'_{min} = x_{min} - \delta \quad (2)$$

$$y'_{min} = y_{min} - \delta \quad (3)$$

$$x'_{max} = x_{max} + \delta \quad (4)$$

$$y'_{max} = y_{max} + \delta \quad (5)$$

It is to be noted that although only a rectangular area was considered as the measurement area in this example, but it is possible to adopt an area expanded by an amount determined by the above expression (1) with respect to the binarized area while maintaining the shape of the area.

Then, an actual area of the minute point as a physical object corresponding to the binarized area is calculated from the number of pixels and the magnification of the optical system, and this is determined as D. Here, the following expression (6) is calculated based on a standard area $D_0$ of the minute point set when creating the bio chip 24 and the measured area D of the minute point.

$$\sigma = D_0/D \quad (6)$$

At this moment, when the minute point 25 is not covered with the foreign matter as indicated by the divided image 106, $\sigma \approx 1$ is obtained. However, when the minute point is covered with the foreign matter as indicated by the divided image 107, $\sigma \gg 1$ is obtained. The intensity measurement is carried out by using this $\sigma$ only when, e.g., $\sigma < 10$. In case of no matching, it is determined that it is the foreign matter or a defect of the minute point itself and data concerning that minute point does not have the reliability.

The following processing is carried out with respect to the divided image 106.

Figure 13B:
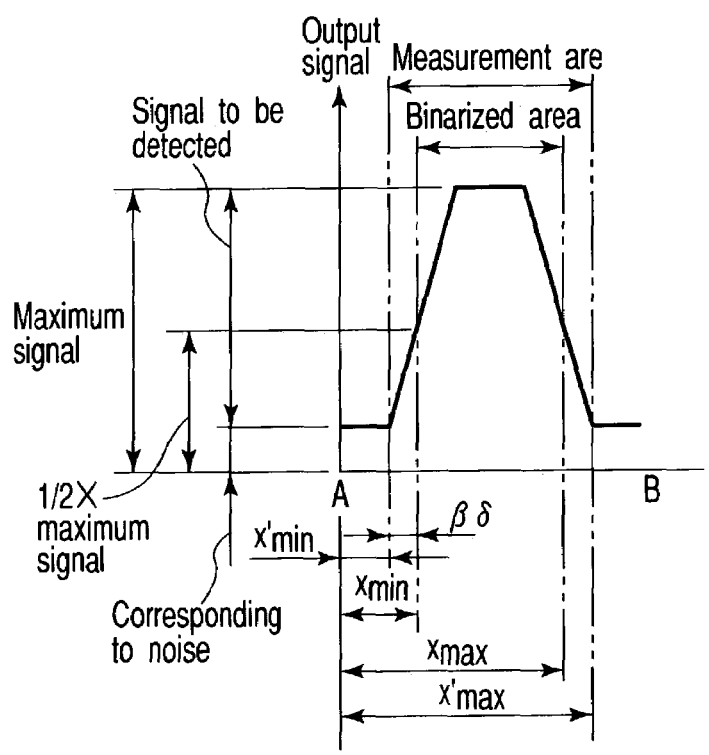
FIG. 13B is a view showing an output signal from a CCD on a line segment AB depicted in FIG. 13A.

That is, as shown in FIG. 13B, the image signal obtained from the CCD element 18 usually contains the noises. Although this noise component is dependent on an apparatus structure or a measurement environment, the excitation light noise (noise caused due to the excitation light) based on the reflected light of the excitation light on the substrate (bio chip 24) or self-light emission of the substrate using the excitation light is dominant, and the stray light noise (noise caused due to the light source other than the excitation light) cannot be ignored in some cases. It is to be noted that FIGS. 13A and 13B show the modeled elements for better understanding, but actually the signal to be detected and the noise signal are not flat, and there are irregularities depending on each position. In particular, the above-described excitation light noise reflects the illumination irregularities, and hence this noise can be the greatest factor of irregularities in the noise component.

Therefore, in this embodiment, an area which is within the divided image area and out of the measurement area is determined as a noise sampling area, and an average noise signal which can be obtained by dividing a sum total of signals in the noise sampling area by an area of the noise sampling area is subtracted from the signals relative to pixels in the measurement area.

Then, a sum total of the detection signals obtained by subtraction in the measurement area is determined as a signal intensity $P_0$ of the minute point. Further, the signal intensity $P_0$ of the minute point is corrected by an actual area of the minute point (normalization processing), and the result is determined as an intensity measurement value P of the minute point, and this P is calculated by the following expression (7). It is to be noted that $D_0$ is a standard area of the minute point and D is an actual area obtained from the binarized image of each minute point calculated in advance in this example.

$$P = (D_0/D)P_0 \quad (7)$$

This correction, i.e., the normalization processing can eliminate the noise caused due to a minute point formation error, or an error when a part of the minute point 25 is hidden by the foreign matter.

It is to be noted that the image of the bio chip 24 is collectively shot by electrical scanning using the CCD element 18 such as one used in this embodiment and it is stored in the image memory, but the present invention is not restricted thereto, the image of the bio chip 24 may be of course divided and shot by performing mechanical scanning like the prior art, thereby obtaining an entire image of the bio chip 24 on the image memory. Furthermore, combining the both methods enables use of a large bio chip which can not be entirely imaged at a time by the CCD element 18.

Moreover, this embodiment has the following inherent advantages as well as the advantages of this invention.

That is, since the CCD element 18 is used, the image of the bio chip 24 can be collectively processed, thereby shortening the measurement time. In addition, on the other hand, since an exposure time can be prolonged, this embodiment is advantageous in the measurement sensitivity of the intensity. It is to be noted that each structure in this embodiment can be of course modified and changed in many ways. For example, as the image processing apparatus, a personal computer can be used. Also, as the CCD element 18, it is possible to use a cooled CCD which is of a type cooled by a Peltier element or the like.

Furthermore, by expanding the foreign matter area and eliminating it from the fluorescent image of the minute point, an error concerning focusing of the optical system can be absorbed, thereby further reducing the influence of the noise light of the foreign matter from the fluorescent image of the minute point.

Moreover, in this embodiment, even if the binarized area does not have a circular shape such as shown in the drawing due to irregularities in the signal to be detected, or even if a plurality of the binarized areas exist in one divided image, determining a rectangular area defined by $(x'_{min}, y'_{min})$ and $(x'_{max}, y'_{max})$ as the measurement area can guarantee that all the signals to be detected are included in this measurement area.

In addition, since the noise sampling area is set in the vicinity of the minute point and the signal intensity of the minute point is corrected, the detection accuracy of the signal to be detected can be improved. Additionally, since the measurement area is set taking defocusing into consideration as described above, it is apparent that the defocusing noise is not generated.

SECOND EMBODIMENT

Figure 16:
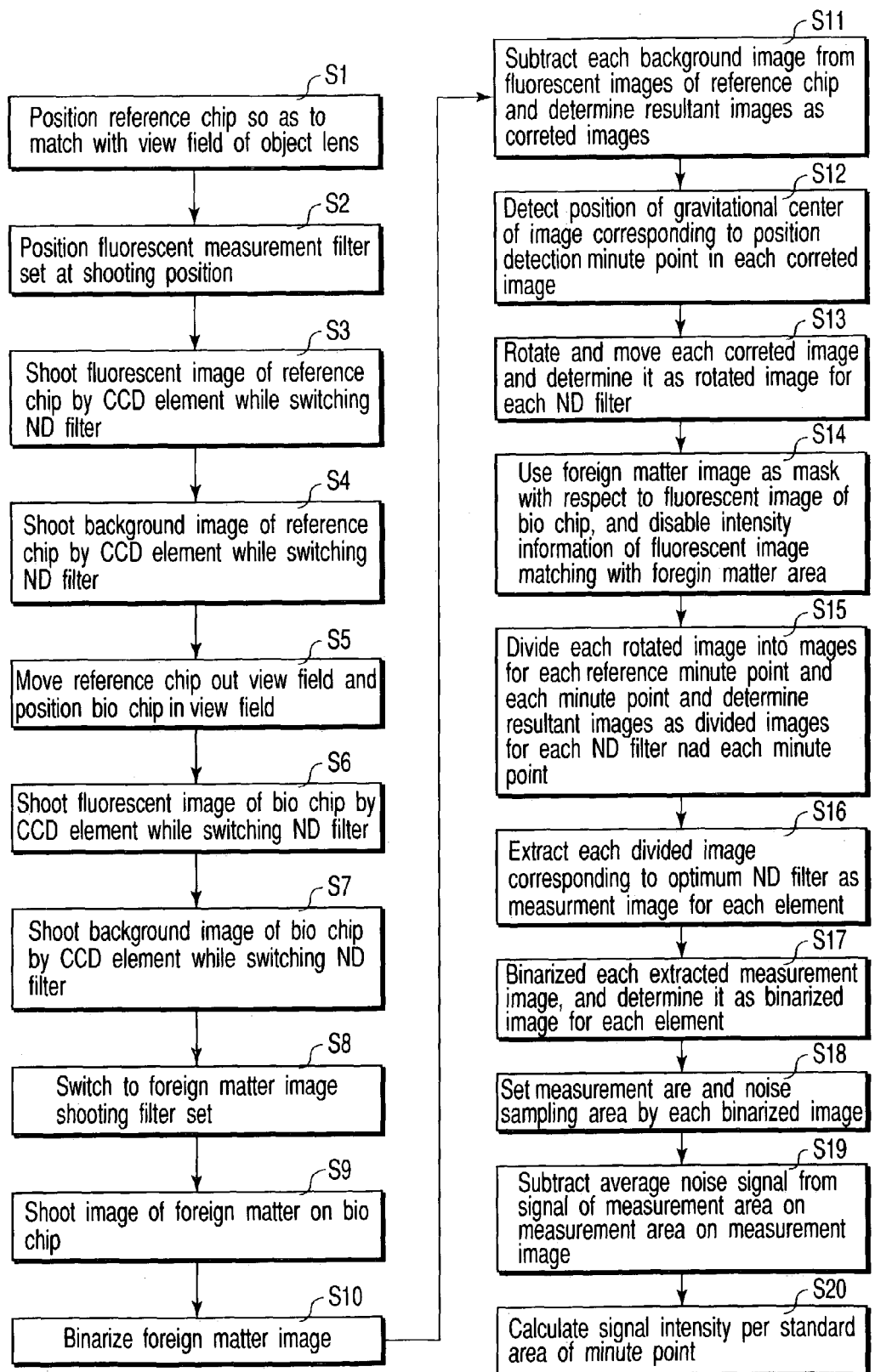
FIG. 16 is a flowchart showing a measuring method according to the second embodiment.
Figure 17:
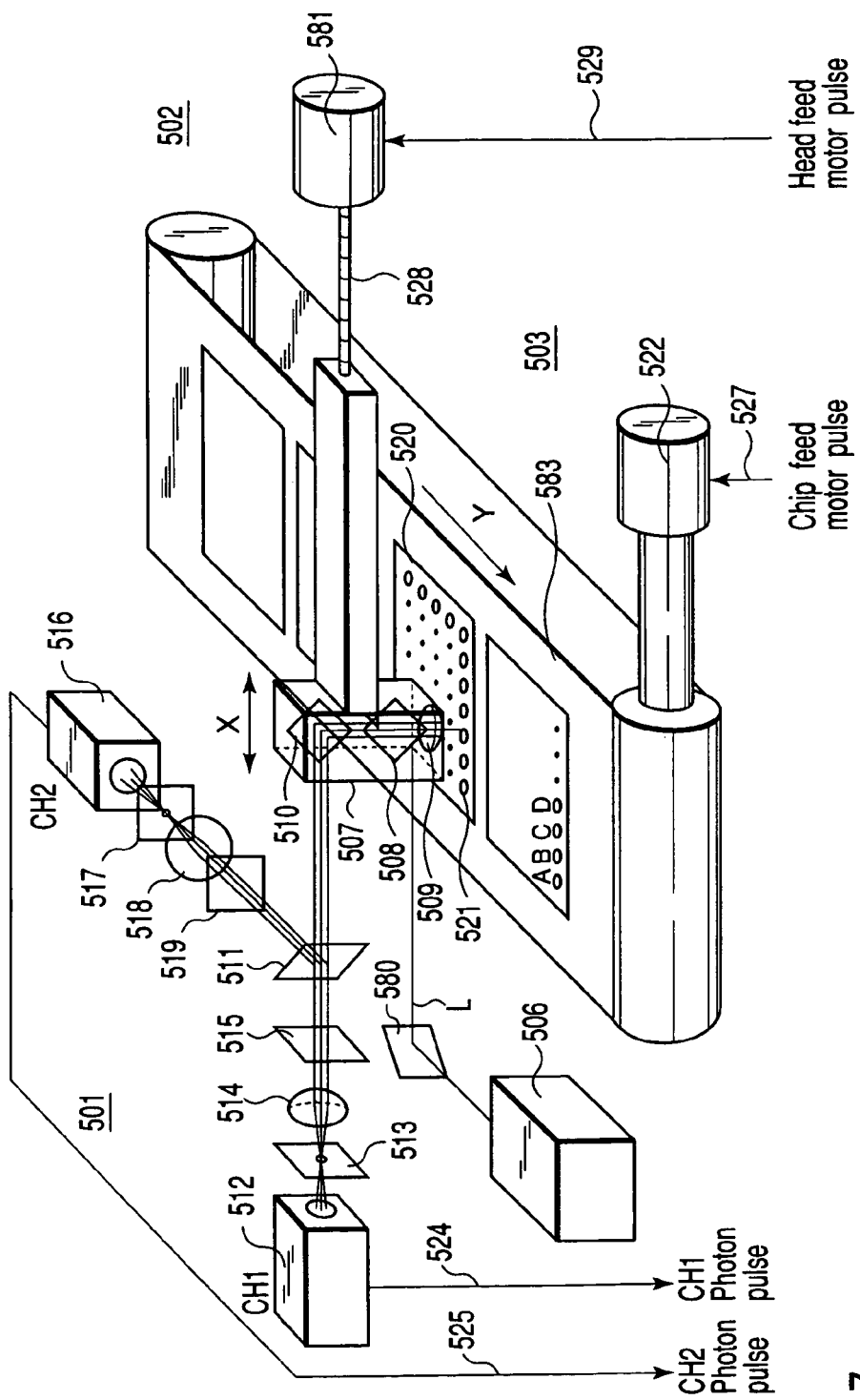
FIG. 17 is a schematic block diagram showing a prior art fluorescent intensity measuring apparatus.

A fluorescent intensity measuring method and apparatus according to a second embodiment of the present invention will now be described with reference to FIGS. 14 and 16.

Figure 14:
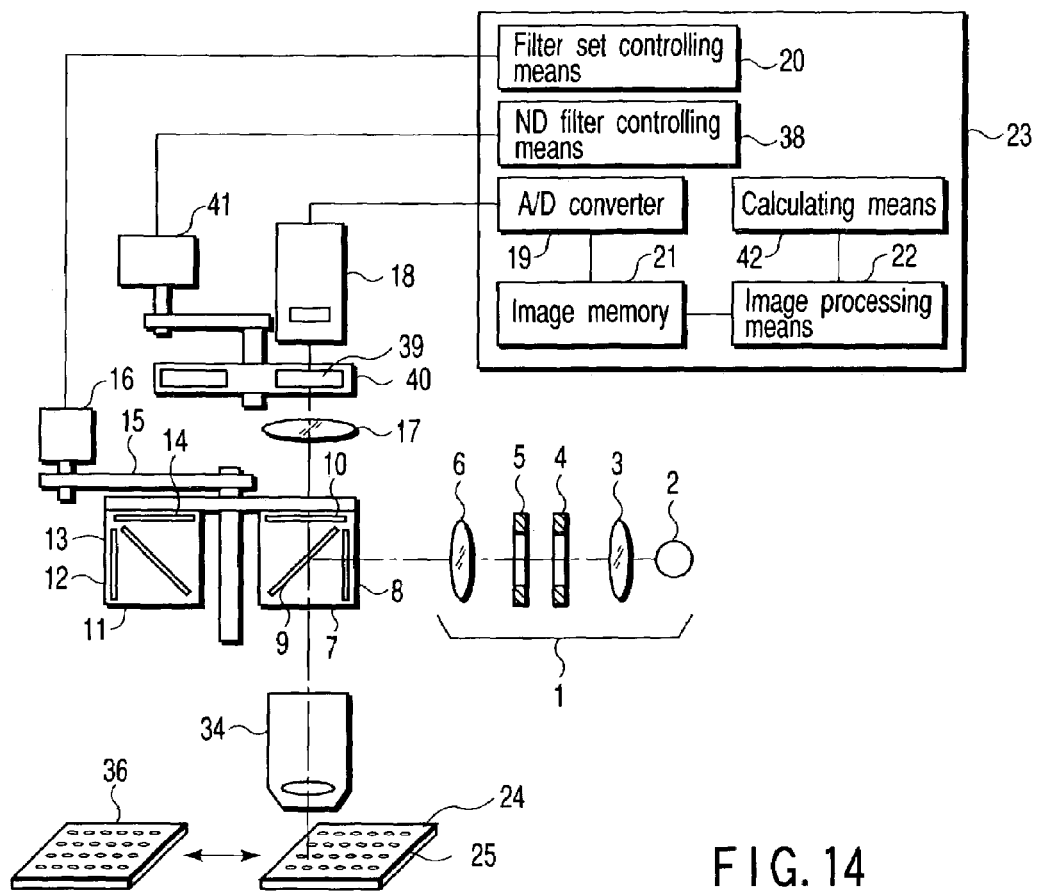
FIG. 14 is a block diagram showing an outline of a fluorescent intensity measuring apparatus according to a second embodiment of the present invention.
Figure 15:
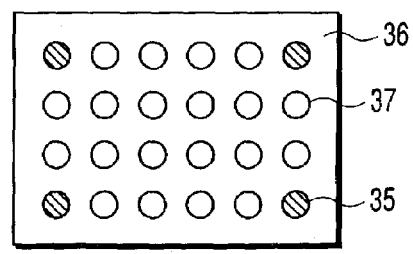
FIG. 15 is a schematic view showing a reference chip.

It is to be noted that FIG. 14 is a block diagram showing an outline of the fluorescent intensity measuring apparatus according to the second embodiment, and FIG. 15 is a schematic view showing a reference chip. Further, FIG. 16 is a flowchart showing a measuring method according to this embodiment.

In this embodiment, as shown in FIG. 14, for the purpose of adjusting a quantity of the light entering the CCD element 18, a plurality of ND filters 39 each having a known transmissivity are selectively inserted on the light path between the image formation lens 17 and the CCD element 18. That is, a plurality of the ND filters 39 are attached to filter holding means 40, and the ND filter with a different transmissivity to be inserted into the light path is switched based on a command from ND filter controlling means 38 by ND filter switching means 41.

Furthermore, in this embodiment, a reference chip 36 shown in FIG. 15 is also used in addition to the bio chip 24 illustrated in FIG. 3. Here, on the reference chip 36, the fluorescent substance used as a fluorescence label on a substrate such as a flat glass is transferred and fixed as reference minute points 37 having the known number of fluorescent molecules at the same positions of the minute points 25 of the bio chip 24, and the same fluorescent molecules as the label are transferred and fixed as position detection minute points 35 at four corners of the minute point group like the bio chip 24.

It is to be noted that the transferring and fixing method specifies the number of fluorescent molecules to be used from a weight of the fluorescent molecules to be used and its quantity of molecules, makes a solution of the fluorescent molecules having this number of fluorescent molecules so as to obtain a specified quantity, and discharge only a fixed quantity of this solution onto the substrate by the ink jet method. Moreover, it is possible to adopt a method to bring the fluorescent substance into contact with the substrate by causing the solution to adhere to a pin. It is to be noted that the number of fluorescent molecules per reference minute point is calculated from various quantities (a quantity of the solution and the number of fluorescent molecules in the solution) and a discharge quantity of the solution. In addition, as a method of holding the fluorescent molecules, using a solid phased reagent enables secure holding of the fluorescent molecules, but it is not necessary required.

This reference chip 36 is set in the same flat plane as the bio chip 24 on a non-illustrated two-axial stage as shown in FIG. 14, and it can be positioned in a view field of the optical system by the two-axial stage.

Since any other structure is the same as the above-described first embodiment, its explanation will be eliminated.

Description will now be given as to the measuring method using the fluorescent intensity measuring apparatus having such a structure with reference to a flowchart of FIG. 16.

First, the reference chip 36 is positioned so as to match with the view field of the object lens 34 (step S1).

That is, the reference chip 36 is positioned by the non-illustrated two-axial stage in such a manner that a measurement range defined by the four positioning minute points 35 on the reference chip 36 is included in a view field range determined by an image magnification of an observation optical system and a light receiving surface size of the CCD element 18.

Then, a fluorescent measurement filter set 7 is positioned at a shooting position (step S2).

That is, a filter set switching mechanism 16 is used to position the fluorescent measurement filter set 7 at the shooting position so as to shoot the fluorescent image of the reference minute points 37 on the reference chip 36.

Then, the fluorescent image of the reference chip 36 is shot by the CCD element 18 while switching the ND filters 39 (step S3).

That is, the reference chip 36 is subjected to excitation illumination, and an image of the fluorescence generated by the fluorescent molecules in the reference minute points 37 is shot while switching a plurality of the ND filters 39. It is to be noted that the CCD element 18 is used as the light receiving element in this embodiment, but the present invention is not restricted to the CCD element, and any other area sensor may be adopted. Therefore, the "CCD element" described below can be substituted by an area sensor.

Subsequently, a background image of the reference chip 36 is shot by the CCD element 18 while switching the ND filters 39 (step S4).

That is, the excitation illumination is interrupted immediately after shooting the fluorescent image of the reference chip 36, and the background image is shot. This background image is constituted by a dark current and a stray light beam which are not required for the detection intensity.

Then, the reference chip 36 is moved out of the view field, and the bio chip 24 is positioned in the view field (step S5).

That is, the bio chip 24 is positioned by the non-illustrated two-axial stage in such a manner that the four positioning minute points 35 on the bio chip 24 substantially match with the positions of the positioning minute points 35 of the reference chip 36.

Then, the fluorescent image of the bio chip 24 is shot by the CCD element 18 while switching the ND filters 39 (step S6).

That is, the bio chip 24 is subjected to excitation illumination, and an image of the fluorescence generated by the fluorescent molecules in each minute point is shot by the CCD element 18. At this moment, the fluorescent image is shot while switching a plurality of the ND filters 39.

Then, a background image of the bio chip 24 is shot by the CCD element 18 while switching the ND filters 39 (step S7).

That is, the excitation illumination is interrupted immediately after shooting the fluorescent image of the bio chip 24, and the background image is shot. This background image is constituted by a dark current and a stray light beam which are not required for the detection intensity like the background image of the reference chip 36.

Subsequently, the filter is switched to the foreign matter image shooting filter set 11 (step S8).

That is, the filter set switching mechanism 16 is used to position the foreign matter image shooting filter set 11 at a shooting position so as to shoot an image of the foreign matter on the bio chip 24.

Thereafter, an image of the foreign matter on the bio chip is shot (step S9).

That is, the foreign matter on the bio chip 24 is illuminated by the light with a wavelength by which the labelling fluorescent substance is not excited, and an image of the foreign matter is shot by the CCD element 18 by using the fluorescence generated by the foreign matter (self-light emission) or the reflected light.

Then, the foreign matter image is binarized (step S10).

That is, the shot foreign matter image or its differential image is binarized by using a specific threshold value, the foreign matter area is specified, and this image is determined as a binarized foreign matter image.

Subsequently, the respective background images are subtracted from the fluorescent images of the reference chip 36 and the bio chip 24, thereby obtaining corrected images (step S11).

That is, generally, an output from the light receiving element includes direct-current noise such as dark current noise or stray light noise. In order to eliminate this direct-current noise, the background images are subtracted from the respective fluorescent images of the reference chip 36 and the bio chip 24, and resultant images are referred to as corrected images which will be targets of the subsequent processing. This is carried out in accordance with each ND filter.

Thereafter, a position of the gravitational center of the image corresponding to the position detection minute point in each corrected image is detected (step S12).

That is, the minute points 25 and the reference minute points 37 formed on the reference chip 36 and the bio chip 24 are two-dimensionally arranged as shown in FIGS. 3 and 15, and four minute points positioned at the four corners are all used as the position detection minute points 35. Since the position detection minute points 35 are used to output position signals, any substance in that element can suffice as long as it is a luminescent substance or a reflection substance. However, it is preferable to use the fluorescent substance with the fluorescent wavelength different from the fluorescent wavelength of the fluorescent substance used as a label. That is because it can eliminate the possibility that the fluorescence generated from the position detection minute points 35 acts as noise. In this case, illumination is carried out by the excitation wavelength inherent to the position detection minute points 35 and positional detection is effected. As to positional detection, there is adopted a method of determining a gravitation center coordinate of each of the four position detection minute points 35 as a position coordinate, or a method of binarizing the corrected image by using a level of ½ of the maximum intensity and determining the four centroids as position coordinates, or the like.

In addition, each corrected image is rotated and moved, thereby obtaining a rotation image for each ND filter (step S13).

That is, the position coordinates are corrected in such a manner that a quadrangle formed by the position coordinates of the four position detection minute points 35 respectively obtained relative to the reference chip 36 and the bio chip 24 becomes a rectangle with the minimum deflection, and the corrected images are rotated and moved with the center of each image at the center of rotation so that each side of this rectangle becomes parallel with the coordinate axis of each image. An image obtained after movement is referred to as a rotated image. At this moment, the binarized foreign matter image is also rotated and moved by the same amount as the bio chip 24.

Then, with the binarized foreign matter image being used as a mask with respect to the fluorescent image of the bio chip 24, the intensity information of the fluorescent image matching with the foreign matter area is disabled (step S14).

That is, logical multiplication of the image obtained as the binarized foreign matter image by and the fluorescent image of the bio chip 24 is carried out the image processing means 22, and intensity data of the pixels of the fluorescent image of the bio chip 24 matching with the binarized foreign matter area is set to "0".

Thereafter, each rotated image is divided into images for each reference minute point 37 and each minute point 25, and the resultant images are determined as the divided image for each ND filter and each minute point (step S15).

That is, the division conditions are determined based on the position coordinates of the four positioning minute points concerning each rotated image of the reference chip 36 and the bio chip 24 and the arrangement conditions of the reference minute points 37 and the reference points 25, and all the rotated images are divided into images for each reference minute point 37 or each minute point 25 under the division conditions, thereby obtaining the divided images.

Then, each divided image corresponding to an optimum ND filter 39 is extracted as a measurement image for each element (step S16).

That is, one reference divided image whose maximum signal intensity falls within a dynamic range of the CCD element 18 and whose intensity signal is maximum is extracted from the reference divided image whose number corresponds to the number of the ND filters with respect to the reference minute points 37 at the same positions on the reference chip 36, and this is referred to as a measurement reference image. Likewise, one divided image whose maximum signal intensity falls within a dynamic range of the CCD element 18 and whose signal intensity is maximum is extracted from the divided images whose number corresponds to the number of the ND filters relative to the minute points 25 at the same positions on the bio chip 24, and this is referred to as a measurement sample image. As to the measurement reference image and the measurement sample image, the corrected intensity $R_k$(=the maximum intensity in the divided image×the transmissivity of the ND filter 39 used for shooting) is obtained in the descending order of the transmissivity $T_k$ of each ND filter 39 used for shooting. In this example, k is a number given to each ND filter in the descending order of the transmissivity (k=1 to n). When a change ratio of $R_k(=(P_{k+1}/T_{k+1})-(P_k/T_k))$ satisfies the negative condition, an image corresponding to the ND filter number k is extracted.

Then, each extracted measurement image is binarized, thereby obtaining the binarized image for each element (step S17).

That is, all of the measurement reference images and the measurement sample images are binarized with an average value of the maximum signal and the minimum signal in each image being determined as a threshold value, and the resultant images are determined as reference binarized images and sample binarized images. Here, as to the sample binarized image, an area D of the binarized area is calculated.

Thereafter, the measurement area and the noise sampling area are set by using each binarized image (step S18).

That is, with respect to all of the reference binarized images, a maximum X coordinate $x_{Rmax}$, a minimum X coordinate $x_{Rmin}$, a maximum Y coordinate $y_{Rmax}$ and a minimum Y coordinate $y_{Rmin}$ of each image are obtained. Likewise, with respect to all of the sample binarized images, a maximum X coordinate $x_{Smax}$, a minimum X coordinate $x_{Smin}$, a maximum Y coordinate $y_{Smax}$ and a minimum Y coordinate $y_{Smin}$ of each image are obtained, and then $x'_{Rmax}$, $x'_{Rmin}$, $y'_{Rmax}$, $y'_{Rmin}$, $s'_{Smax}$, $x'_{Smin}$, $y'_{Smax}$ and $y'_{Smin}$ used to set the sampling area of the noise are calculated by using the following expressions.

$$x'_{min} = x_{min} - \delta \quad (8)$$

$$y'_{min} = y_{min} - \delta \quad (9)$$

$$x'_{max} = x_{max} + \delta \quad (10)$$

$$y'_{max} = y_{max} + \delta \quad (11)$$

In the above expression, δ is a quantity which gives a blur quantity of the optical system, and it is given by the following expression.

$$\delta = \beta \cdot \left(1.619 \frac{\lambda}{\alpha} + \alpha |\Delta|\right) \quad (12)$$

It is to be noted that β is an image magnification of the optical system, λ is a wavelength of the light used to form images of the minute points 25 and the reference minute points 37, α is a numerical aperture of the object lens 34 on the bio chip side, and Δ is a defocusing quantity.

The inside of a rectangle defined by the point ($x'_{Rmin}$, $y'_{Rmin}$) and the point ($x'_{Rmax}$, $y_{Rmax}$) calculated herein is determined as the measurement area of the measurement reference image, and the outside of the rectangle is determined as the noise sampling area of the measurement reference image. Likewise, the inside of a rectangle defined by the point ($x'_{Smin}$, $y'_{Smin}$) and the point ($x'_{Smax}$, $y'_{Smax}$) is determined as the measurement area of the measurement sample image, and the outside of the rectangle is determined as the noise sampling area of the measurement sample.

Subsequently, an average noise signal is subtracted from the signal of the measurement area on the measurement image (step S19).

That is, the noise per unit area is obtained from the signal in the noise sampling area set in the measurement reference image, this signal is subtracted from the signal of the measurement area in the measurement reference image, and a result is determined as a detection signal of the measurement reference image. Likewise, the noise per unit area is obtained from the signal of the noise sampling area set in the measurement sample image, this signal is subtracted from the signal of the measurement area in the measurement sample image, and a result is determined as a detection signal of the measurement sample image.

Then, a signal intensity per standard area of the minute point 25 is calculated (step S20).

That is, a sum total of the detection signals in the measurement areas of the measurement reference image corresponding to each reference minute point 36 is calculated, and this is determined as $P_R$. Furthermore, a maximum value of the sum total $P_R$ of the detection signals corresponding to a plurality of the minute points 25 is determined as $P_{Rmax}$. Moreover, a sum total of the detection signals in the measurement area of the measurement sample image corresponding to each minute point 25 is calculated, and this is determined as $P_{D0}$. Then, the signal intensity $P_D$ per standard area of the minute point 25 is calculated by using the following expression (13). These signal intensities are obtained as intensities with intensity error generated due to excitation light irregularities, excitation light noises and minute point formation errors being removed therefrom.

$$P_D = \frac{D_0}{D} \cdot \frac{P_R}{P_{R\max}} P_{D0} \tag{13}$$

According to this embodiment described above, since the excitation light quantity is corrected by using the reference chip 36 when measuring the intensity of the bio chip 24, spatial and temporal fluctuations in the excitation light can be cancelled.

Although the present invention has been described based on the embodiments, the present invention is not restricted to the foregoing embodiment, and various modifications or applications can be of course enabled within the scope of the present invention.

Here, the summary of the present invention is as follows.

(1) There is provided a fluorescent intensity measuring method which measures the intensity of minute points which are arranged on a substrate having a substantially flat surface and include a fluorescent substance, comprising:

a first imaging step of emitting light with a wavelength with which the fluorescent substance can be excited and obtaining an image of the minute point including the fluorescent substance as a first image;

a second imaging step of obtaining an image of foreign matter which has adhered on the substrate as a second image by light with a wavelength with which the fluorescent substance is not excited;

an extraction step of obtaining a binarized image by extracting a foreign matter area from the second image; and a foreign matter elimination step of disabling an image at a part overlapping the foreign matter area in the first image with the binarized image being used as a mask.

The first embodiment and the second embodiment correspond to embodiments concerning this invention.

There is obtained the first image by emitting light with a wavelength which excites the labelling fluorescent substance, a mask is created from the foreign matter area image extracted from the image of the foreign matter which has adhered to the measurement object obtained by emitting light with a wavelength which does not excite the fluorescent substance, and a logical product of the mask and the first image is calculated, thereby eliminating the foreign matter area from the first image. Therefore, the noise light from the foreign matter which has adhered to the bio chip can be removed.

Errors in intensity measurement can be reduced.

(2) There is provided a fluorescent intensity measuring method according to (1), further comprising an expansion step of expanding the foreign matter area of the binarized image by a determined quantity.

The first embodiment and the second embodiment correspond to the embodiments concerning the present invention.

A mask is created by applying the expansion processing to the foreign matter area by only a distance obtained by considering an optical blur quantity with respect to the foreign matter area acquired by applying the binarization processing to the image of the foreign mater adhering to the measurement object, the image of which is obtained by emitting light with a wavelength which does not excite the fluorescent substance, and a logical product of the mask and the first image obtained by emitting excitation light with a wavelength which excites the labelled fluorescent substance is calculated.

Since the foreign matter area is expanded, measurement errors do not become large even if the focusing accuracy of the observation optical system is poor.

(3) There is provided a fluorescent intensity measuring method according to (1) or (2), further comprising a normalization step of normalizing the measured intensity of the minute point by using a reference area of the minute point.

The first embodiment corresponds to the embodiment concerning the present invention.

The intensity of pixels in the minute point is integrated, and the intensity measurement value is normalized based on the reference area of the minute point.

Even if there are irregularities in area of the minute point, errors in the intensity measurement value become small.

(4) There is provided a fluorescent intensity measuring method according to any of (1) to (3), further comprising a reliability judgment step of obtaining an area of each minute point after the foreign matter elimination step and judging the reliability of the measurement value based on a ratio of the area and the reference area of the minute point.

The first embodiment corresponds to the embodiment concerning the present invention.

A ratio of an actual area relative to the reference area is calculated from the reference area of the minute point and the actual area of the minute point, and a result is compared with a preset threshold value.

The reliability of the measurement value can be quantitatively judged.

(5) There is provided a fluorescent intensity measuring method according to any of (1) to (4), further comprising a correction step of correcting the second image by using a reference image.

The first embodiment corresponds to the embodiment concerning the present invention.

The reference image is used to measure irregularities in the excitation light, thereby correcting the second image.

Even if there are spatial irregularities in the excitation light, all the foreign matter can be correctly recognized.

(6) There is provided a fluorescent intensity measuring method according to any of claims (1) to (4), wherein the extraction step obtains the binarized image by using a differential image acquired from the second image.

The first embodiment corresponds to the embodiment concerning the present invention.

The differential image obtained from the second image is used to extract a foreign matter area from the second image, thereby acquiring the binarized image.

Even if there are spatial irregularities in the excitation light, all the foreign matter can be correctly recognized without using the reference image.

(7) There is provided a fluorescent intensity measuring method according to (6), wherein the extraction step determines a binarization level of the binarized image by using a frequency distribution of a differential signal corresponding to each pixel.

The first embodiment corresponds to the embodiment concerning the present invention.

A threshold value for binarization is determined by using a frequency distribution of a differential signal corresponding to each pixel.

An appropriate threshold value can be set.

(8) There is provided a fluorescent intensity measuring method according to (6) or (7), wherein the differential signal is standardized with an intensity in a minute area corresponding to the differential signal.

The first embodiment corresponds to the embodiment concerning the present invention.

The differential signal is standardized with an intensity in a minute area corresponding to the differential signal, and a threshold value for binarization is set based the standardized signal.

The further appropriate threshold value can be set, and a plurality of types of foreign matters can be correctly recognized.

(9) There is provided a fluorescent intensity measuring apparatus which measures the intensity of a fluorescent image obtained by irradiating minute points which are arranged on a substrate having a substantially flat surface and include a fluorescent substance with an excitation light beam, comprising:

a light source;
first wavelength selecting means for selecting a wavelength of the excitation light;
image forming means for forming an image of the fluorescent substance;
second wavelength selecting means for selecting only a wavelength of a generated fluorescence;
photoelectric converting means for obtaining an image by scanning the fluorescent image;
storing means for storing the image; and
image processing means for performing:

processing to emit light with a wavelength which can excite the fluorescent substance in the light from the light source by controlling the first wavelength selecting means, to obtain an image of the minute point including the fluorescent substance as a first image by the photoelectric converting means by controlling the second wavelength selecting means, and to store the first image in the storing means;

processing to emit light with a wavelength which does not excite the fluorescent substance in the light from the light source by controlling the first wavelength selecting means, obtain an image of a foreign matter adhering to the substrate as a second image by the photoelectric converting means by controlling the second wavelength selecting means, and to store the second image in the storing means;

processing to obtain a binarized image by extracting a foreign matter area from the second image stored in the storing means; and processing to disable an image at a part overlapping the foreign matter area in the first image stored in the storing means with the binarized image being used as a mask.

The first embodiment corresponds to the embodiment concerning the present invention.

The first image is obtained by emitting light with a wavelength which excites the labelling fluorescent substance, a mask is created by using the foreign matter area image extracted from the image of the foreign matter adhering to the measurement object obtained by emitting light with a wavelength which does not excite the fluorescent substance, and logical multiplication of the mask and the first image is executed, thereby eliminating the foreign matter area from the first image. Therefore, the noise light from the foreign matter adhering to the bio chip can be eliminated.

Errors in the intensity measurement can be reduced.

As described above, the present invention is effective in a technical field of chemical and physical property analysis of a biological material such as a DNA or a protein.

What is claimed is:

1. A fluorescent intensity measuring method which measures the intensity of minute points which are arranged on a substrate having a substantially flat surface and include a fluorescent substance, comprising:

a first imaging step of emitting light with a wavelength with which the fluorescent substance can be excited and obtaining an image of each minute point including the fluorescent substance as a first image;

a second imaging step of obtaining an image of foreign matter adhering on the substrate as a second image by light with a wavelength which does not excite the fluorescent substance;

an extraction step of obtaining a binarized image by extracting a foreign matter area from the second image;

a foreign matter elimination step of disabling an image at a part overlapping the foreign matter area in the first image with the binarized image being used as a mask;

an expansion step of expanding the foreign matter area of the binarized image by a determined quantity;

a normalization step of normalizing the measured intensity of the minute point by using a reference area of the minute point; and a reliability judgment step of obtaining an area of each minute point after the foreign matter elimination step and judging the reliability of the measurement value by using a ratio of the obtained area and the reference area of the minute point.

2. A fluorescent intensity measuring method according to claim 1, further comprising a correction step of correcting the second image by using a reference image.

3. A fluorescent intensity measuring method according to claim 1, wherein the extraction step obtains the binarized image by using a differential image acquired from the second image.

4. A fluorescent intensity measuring method according to claim 3, wherein the extraction step determines a binarization level of the binarized image by using a frequency distribution of the differential signal corresponding to each pixel.

5. A fluorescent intensity measuring method according to claim 4, wherein the differential signal is standardized with an intensity in a minute area corresponding to the differential signal.

6. A fluorescent intensity measuring method according to claim 3, wherein the differential signal is standardized with an intensity in a minute area corresponding to the differential signal.

7. A fluorescent intensity measuring method which measures the intensity of minute points which are arranged on a substrate having a substantially flat surface and include a fluorescent substance, comprising:
- a first imaging step of emitting light with a wavelength with which the fluorescent substance can be excited and obtaining an image of each minute point including the fluorescent substance as a first image;
- a second imaging step of obtaining an image of foreign matter adhering on the substrate as a second image by light with a wavelength which does not excite the fluorescent substance;
- an extraction step of obtaining a binarized image by extracting a foreign matter area from the second image;
- a foreign matter elimination step of disabling an image at a part overlapping the foreign matter area in the first image with the binarized image being used as a mask;
- an expansion step of expanding the foreign matter area of the binarized image by a determined quantity;
- a normalization step of normalizing the measured intensity of the minute point by using a reference area of the minute point; and
- a correction step of correcting the second image by using a reference image.

8. A fluorescent intensity measuring method which measures the intensity of minute points which are arranged on a substrate having a substantially flat surface and include a fluorescent substance, comprising:
- a first imaging step of emitting light with a wavelength with which the fluorescent substance can be excited and obtaining an image of each minute point including the fluorescent substance as a first image;
- a second imagine step of obtaining an image of foreign matter adhering on the substrate as a second image by light with a wavelength which does not excite the fluorescent substance;
- an extraction step of obtaining a binarized image by extracting a foreign matter area from the second image;
- a foreign matter elimination step of disabling an image at a part overlapping the foreign matter area in the first image with the binarized image being used as a mask;
- an expansion step of expanding the foreign matter area of the binarized image by a determined quantity; and
- a normalization step of normalizing the measured intensity of the minute point by using a reference area of the minute point;
- wherein the extraction step obtains the binarized image by using a differential image acquired from the second image.

9. A fluorescent intensity measuring method according to claim 8, wherein the extraction step determines a binarization level of the binarized image by using a frequency distribution of the differential signal corresponding to each pixel.

10. A fluorescent intensity measuring method according to claim 9, wherein the differential signal is standardized with an intensity in a minute area corresponding to the differential signal.

11. A fluorescent intensity measuring method according to claim 8, wherein the differential signal is standardized with an intensity in a minute area corresponding to the differential signal.

12. A fluorescent intensity measuring method which measures the intensity of minute points which are arranged on a substrate having a substantially flat surface and include a fluorescent substance, comprising:
- a first imaging step of emitting light with a wavelength with which the fluorescent substance can be excited and obtaining an image of each minute point including the fluorescent substance as a first image;
- a second imaging step of obtaining an image of foreign matter adhering on the substrate as a second image by light with a wavelength which does not excite the fluorescent substance;
- an extraction step of obtaining a binarized image by extracting a foreign matter area from the second image;
- a foreign matter elimination step of disabling an image at a part overlapping the foreign matter area in the first image with the binarized image being used as a mask;
- an expansion step of expanding the foreign matter area of the binarized image by a determined quantity; and
- a reliability judgment step of obtaining an area of each minute point after the foreign matter elimination step and judging the reliability of the measurement value by using a ratio of the obtained area and the reference area of the minute point.

13. A fluorescent intensity measuring method according to claim 12, further comprising a correction step of correcting the second image by using a reference image.

14. A fluorescent intensity measuring method according to claim 12, wherein the extraction step obtains the binarized image by using a differential image acquired from the second image.

15. A fluorescent intensity measuring method according to claim 14, wherein the extraction step determines a binarization level of the binarized image by using a frequency distribution of the differential signal corresponding to each pixel.

16. A fluorescent intensity measuring method according to claim 15, wherein the differential signal is standardized with an intensity in a minute area corresponding to the differential signal.

17. A fluorescent intensity measuring method according to claim 14, wherein the differential signal is standardized with an intensity in a minute area corresponding to the differential signal.

18. A fluorescent intensity measuring method which measures the intensity of minute points which are arranged on a substrate having a substantially flat surface and include a fluorescent substance, comprising:

a first imaging step of emitting light with a wavelength with which the fluorescent substance can be excited and obtaining an image of each minute point including the fluorescent substance as a first image;

a second imaging step of obtaining an image of foreign matter adhering on the substrate as a second image by light with a wavelength which does not excite the fluorescent substance;

an extraction step of obtaining a binarized image by extracting a foreign matter area from the second image;

a foreign matter elimination step of disabling an image at a part overlapping the foreign matter area in the first image with the binarized image being used as a mask; and an expansion step of expanding the foreign matter area of the binarized image by a determined quantity;

wherein the extraction step obtains the binarized image by using a differential image acquired from the second image.

19. A fluorescent intensity measuring method according to claim 18, wherein the extraction step determines a binarization level of the binarized image by using a frequency distribution of the differential signal corresponding to each pixel.

20. A fluorescent intensity measuring method according to claim 19, wherein the differential signal is standardized with an intensity in a minute area corresponding to the differential signal.

21. A fluorescent intensity measuring method according to claim 18, wherein the differential signal is standardized with an intensity in a minute area corresponding to the differential signal.

22. A fluorescent intensity measuring method which measures the intensity of minute points which are arranged on a substrate having a substantially flat surface and include a fluorescent substance, comprising:

a first imaging step of emitting light with a wavelength with which the fluorescent substance can be excited and obtaining an image of each minute point including the fluorescent substance as a first image;

a second imaging step of obtaining an image of foreign matter adhering on the substrate as a second image by light with a wavelength which does not excite the fluorescent substance;

an extraction step of obtaining a binarized image by extracting a foreign matter area from the second image;

a foreign matter elimination step of disabling an image at a part overlapping the foreign matter area in the first image with the binarized image being used as a mask;

a normalization step of normalizing the measured intensity of the minute point by using a reference area of the minute point; and a reliability judgment step of obtaining an area of each minute point after the foreign matter elimination step and judging the reliability of the measurement value by using a ratio of the obtained area and the reference area of the minute point.

23. A fluorescent intensity measuring method according to claim 22, further comprising a correction step of correcting the second image by using a reference image.

24. A fluorescent intensity measuring method according to claim 22, wherein the extraction step obtains the binarized image by using a differential image acquired from the second image.

25. A fluorescent intensity measuring method according to claim 24, wherein the extraction step determines a binarization level of the binarized image by using a frequency distribution of the differential signal corresponding to each pixel.

26. A fluorescent intensity measuring method according to claim 25, wherein the differential signal is standardized with an intensity in a minute area corresponding to the differential signal.

27. A fluorescent intensity measuring method according to claim 24, wherein the differential signal is standardized with an intensity in a minute area corresponding to the differential signal.

28. A fluorescent intensity measuring method which measures the intensity of minute points which are arranged on a substrate having a substantially flat surface and include a fluorescent substance, comprising:

a first imaging step of emitting light with a wavelength with which the fluorescent substance can be excited and obtaining an image of each minute point including the fluorescent substance as a first image;

a second imaging step of obtaining an image of foreign matter adhering on the substrate as a second image by light with a wavelength which does not excite the fluorescent substance;

an extraction step of obtaining a binarized image by extracting a foreign matter area from the second image;

a foreign matter elimination step of disabling an image at a part overlapping the foreign matter area in the first image with the binarized image being used as a mask;

a normalization step of normalizing the measured intensity of the minute point by using a reference area of the minute point; and a correction step of correcting the second image by using a reference image.

29. A fluorescent intensity measuring method which measures the intensity of minute points which are arranged on a substrate having a substantially flat surface and include a fluorescent substance, comprising:

a first imaging step of emitting light with a wavelength with which the fluorescent substance can be excited and obtaining an image of each minute point including the fluorescent substance as a first image;

a second imagine step of obtaining an image of foreign matter adhering on the substrate as a second image by light with a wavelength which does not excite the fluorescent substance;

an extraction step of obtaining a binarized image by extracting a foreign matter area from the second image;

a foreign matter elimination step of disabling an image at a part overlapping the foreign matter area in the first image with the binarized image being used as a mask; and a normalization step of normalizing the measured intensity of the minute point by using a reference area of the minute point;

wherein the extraction step obtains the binarized image by using a differential image acquired from the second image.

30. A fluorescent intensity measuring method according to claim 29, wherein the extraction step determines a binarization level of the binarized image by using a frequency distribution of the differential signal corresponding to each pixel.

31. A fluorescent intensity measuring method according to claim 30, wherein the differential signal is standardized with an intensity in a minute area corresponding to the differential signal.

32. A fluorescent intensity measuring method according to claim 29, wherein the differential signal is standardized with an intensity in a minute area corresponding to the differential signal.

33. A fluorescent intensity measuring method which measures the intensity of minute points which are arranged on a substrate having a substantially flat surface and include a fluorescent substance, comprising:
- a first imaging step of emitting light with a wavelength with which the fluorescent substance can be excited and obtaining an image of each minute point including the fluorescent substance as a first image;
- a second imaging step of obtaining an image of foreign matter adhering on the substrate as a second image by light with a wavelength which does not excite the fluorescent substance;
- an extraction step of obtaining a binarized image by extracting a foreign matter area from the second image;
- a foreign matter elimination step of disabling an image at a part overlapping the foreign matter area in the first image with the binarized image being used as a mask; and
- a reliability judgment step of obtaining an area of each minute point after the foreign matter elimination step and judging the reliability of the measurement value by using a ratio of the obtained area and the reference area of the minute point.

34. A fluorescent intensity measuring method according to claim 33, further comprising a correction step of correcting the second image by using a reference image.

35. A fluorescent intensity measuring method according to claim 33, wherein the extraction step obtains the binarized image by using a differential image acquired from the second image.

36. A fluorescent intensity measuring method according to claim 35, wherein the extraction step determines a binarization level of the binarized image by using a frequency distribution of the differential signal corresponding to each pixel.

37. A fluorescent intensity measuring method according to claim 36, wherein the differential signal is standardized with an intensity in a minute area corresponding to the differential signal.

38. A fluorescent intensity measuring method according to claim 35, wherein the differential signal is standardized with an intensity in a minute area corresponding to the differential signal.

39. A fluorescent intensity measuring method which measures the intensity of minute points which are arranged on a substrate having a substantially flat surface and include a fluorescent substance, comprising:
- a first imaging step of emitting light with a wavelength with which the fluorescent substance can be excited and obtaining an image of each minute point including the fluorescent substance as a first image;
- a second imaging step of obtaining an image of foreign matter adhering on the substrate as a second image by light with a wavelength which does not excite the fluorescent substance;
- an extraction step of obtaining a binarized image by extracting a foreign matter area from the second image; and
- a foreign matter elimination step of disabling an image at a part overlapping the foreign matter area in the first image with the binarized image being used as a mask;
- wherein the extraction step obtains the binarized image by using a differential image acquired from the second image.

40. A fluorescent intensity measuring method according to claim 39, wherein the extraction step determines a binarization level of the binarized image by using a frequency distribution of the differential signal corresponding to each pixel.

41. A fluorescent intensity measuring method according to claim 40, wherein the differential signal is standardized with an intensity in a minute area corresponding to the differential signal.

42. A fluorescent intensity measuring method according to claim 39, wherein the differential signal is standardized with an intensity in a minute area corresponding to the differential signal.

* * * * *